(12) United States Patent
Peterson et al.

(10) Patent No.: US 12,042,149 B2
(45) Date of Patent: Jul. 23, 2024

(54) METHOD AND APPARATUS FOR WOUND CLOSURE WITH SEQUENTIAL TISSUE POSITIONING AND RETENTION

(71) Applicant: Incisive Surgical, Inc., Plymouth, MN (US)

(72) Inventors: James A. Peterson, Edina, MN (US); David B. Herridge, Plymouth, MN (US); Christopher J. Sperry, Plymouth, MN (US); Chad D. Naegeli, Plymouth, MN (US)

(73) Assignee: Incisive Surgical, Inc., Plymouth, MN (US)

( * ) Notice: Subject to any disclaimer, the term of this patent is extended or adjusted under 35 U.S.C. 154(b) by 615 days.

(21) Appl. No.: 17/323,220

(22) Filed: May 18, 2021

(65) Prior Publication Data

US 2021/0267598 A1  Sep. 2, 2021

Related U.S. Application Data

(60) Continuation of application No. 15/843,361, filed on Dec. 15, 2017, now Pat. No. 11,045,195, which is a
(Continued)

(51) Int. Cl.
*A61B 17/10* (2006.01)
*A61B 17/064* (2006.01)
(Continued)

(52) U.S. Cl.
CPC ............ *A61B 17/10* (2013.01); *A61B 17/064* (2013.01); *A61B 17/0682* (2013.01);
(Continued)

(58) Field of Classification Search
CPC ... A61B 17/064; A61B 17/0682; A61B 17/08; A61B 17/10; A61B 2017/00004; A61B 2017/081
See application file for complete search history.

(56) References Cited

U.S. PATENT DOCUMENTS

| 718,649 A | 1/1903 | Morehouse |
| 2,283,814 A | 5/1942 | LaPlace |

(Continued)

FOREIGN PATENT DOCUMENTS

| EP | 0 657 139 | 6/1995 | ........... A61B 17/072 |
| EP | 1 323 384 | 7/2003 | ........... A61B 17/068 |

(Continued)

OTHER PUBLICATIONS

Brochure: Information Booklet for Auto Suture$^{ADDAC\text{-}AGO}$ Purse String Instrument, Auto Suture Company, a division of United States Surgical Corporation, Norwalk, CT, 2 pgs., (1978).
(Continued)

*Primary Examiner* — Ryan J. Severson
(74) *Attorney, Agent, or Firm* — Fish & Richardson P.C.

(57) ABSTRACT

Apparatus and related methods for sequentially positioning and retaining opposing sides of a tissue wound. The apparatus includes a device body having a head portion for positioning between first and second sides of the wound, with the head portion defining first and second retention zones on opposed side of the head portion. The device body further includes first and second approximation arms. The device body further includes a trigger assembly defining three stages of operation. A first stage of operation positions the first approximation arm proximate the first retention zone. A second stage of operation positions the second approximation arm proximate the second retention zone with the first approximation arm remaining in approximation to the first retention zone. A third stage of operation advances a fastener into the first and second retention zones. In this manner, the apparatus sequentially positions the first and second sides with respect to the head portion.

14 Claims, 28 Drawing Sheets

Related U.S. Application Data division of application No. 14/262,071, filed on Apr. 25, 2014, now Pat. No. 9,844,377.

(51) Int. Cl.
  *A61B 17/068* (2006.01)
  *A61B 17/08* (2006.01)
  *A61B 17/00* (2006.01)

(52) U.S. Cl.
  CPC .... *A61B 17/08* (2013.01); *A61B 2017/00004* (2013.01); *A61B 2017/081* (2013.01)

(56) References Cited

U.S. PATENT DOCUMENTS

| | | | |
|---|---|---|---|
| 2,344,071 A | 3/1944 | Wilson et al. |
| 2,351,608 A | 6/1944 | Greenwood |
| 2,439,383 A | 4/1948 | Erickson |
| 2,457,362 A | 12/1948 | Giglio |
| 2,526,902 A | 10/1950 | Rublee |
| 2,881,762 A | 4/1959 | Lowrie |
| 2,959,172 A | 11/1960 | Held |
| 3,074,409 A | 1/1963 | Bielz |
| 3,082,426 A | 3/1963 | Miles |
| 3,123,077 A | 3/1964 | Alcamo |
| 3,297,033 A | 1/1967 | Schmitt et al. |
| 3,344,790 A | 10/1967 | Dorner |
| 3,570,497 A | 3/1971 | Lemole |
| 3,601,302 A | 8/1971 | Potekhina et al. |
| 3,636,956 A | 1/1972 | Schneider |
| 3,638,654 A | 2/1972 | Akuba |
| 3,643,851 A | 2/1972 | Green et al. |
| 3,716,058 A | 2/1973 | Tanner, Jr. |
| 3,757,629 A | 9/1973 | Schneider |
| 3,792,010 A | 2/1974 | Wasserman et al. |
| 3,855,688 A | 12/1974 | Knohl |
| 3,858,783 A | 1/1975 | Kapitanov et al. |
| 4,014,492 A | 3/1977 | Rothfuss |
| 4,027,676 A | 6/1977 | Mattei |
| 4,047,533 A | 9/1977 | Perciaccante et al. |
| 4,162,678 A | 7/1979 | Fedotov et al. |
| 4,164,225 A | 8/1979 | Johnson et al. |
| 4,204,541 A | 5/1980 | Kapitanov |
| 4,217,902 A | 8/1980 | March |
| 4,261,244 A | 1/1981 | Becht et al. |
| 4,259,959 A | 4/1981 | Walker |
| 4,296,751 A | 10/1981 | Blake, III et al. |
| 4,317,451 A | 3/1982 | Cerwin et al. |
| 4,345,601 A | 8/1982 | Fukuda |
| 4,354,628 A | 10/1982 | Green |
| 4,396,139 A | 8/1983 | Hall et al. |
| 4,399,810 A | 8/1983 | Samuels et al. |
| 4,407,286 A | 10/1983 | Noiles et al. |
| 4,410,125 A | 10/1983 | Noiles et al. |
| D271,418 S | 11/1983 | Campbell et al. |
| 4,428,376 A | 1/1984 | Mericle |
| 4,430,998 A | 2/1984 | Harvey et al. |
| 4,434,796 A | 3/1984 | Karapetian et al. |
| 4,440,171 A | 4/1984 | Nomoto et al. |
| 4,454,875 A | 6/1984 | Pratt et al. |
| 4,465,071 A | 8/1984 | Samuels et al. |
| 4,467,805 A | 8/1984 | Fukuda |
| 4,484,580 A | 11/1984 | Nomoto et al. |
| 4,485,816 A | 12/1984 | Krumme |
| 4,485,953 A | 12/1984 | Rothfuss |
| 4,493,322 A | 1/1985 | Becht |
| 4,505,273 A | 3/1985 | Braun et al. |
| 4,506,669 A | 3/1985 | Blake, III |
| D278,656 S | 4/1985 | Green et al. |
| 4,508,253 A | 4/1985 | Green |
| 4,513,746 A | 4/1985 | Aranyi et al. |
| 4,526,173 A | 7/1985 | Sheehan |
| 4,526,174 A | 7/1985 | Froelich |
| 4,534,351 A | 8/1985 | Korthoff |
| 4,534,352 A | 8/1985 | Korthoff |
| 4,535,772 A | 8/1985 | Sheehan |
| 4,539,990 A | 9/1985 | Stivala |
| 4,548,202 A | 10/1985 | Duncan |
| 4,557,265 A | 12/1985 | Andersson |
| 4,566,620 A | 1/1986 | Green et al. |
| 4,568,009 A | 2/1986 | Green |
| 4,570,623 A | 2/1986 | Ellison et al. |
| 4,573,622 A | 3/1986 | Green et al. |
| 4,583,670 A | 4/1986 | Alvarado |
| 4,592,498 A | 6/1986 | Braun et al. |
| 4,593,843 A | 6/1986 | Saravis |
| 4,596,249 A | 6/1986 | Freda et al. |
| 4,596,350 A | 6/1986 | Smith et al. |
| 4,603,693 A | 8/1986 | Conta et al. |
| 4,607,638 A | 8/1986 | Crainich |
| 4,610,251 A | 9/1986 | Kumar |
| 4,618,086 A | 10/1986 | Li et al. |
| 4,619,262 A | 10/1986 | Taylor |
| D287,630 S | 1/1987 | Sharkany et al. |
| 4,637,380 A | 1/1987 | Orejola |
| 4,646,741 A | 3/1987 | Smith |
| 4,655,222 A | 4/1987 | Florez et al. |
| 4,665,916 A | 5/1987 | Green |
| 4,671,279 A | 6/1987 | Hill |
| 4,676,245 A | 6/1987 | Fukuda |
| 4,696,300 A | 9/1987 | Anderson |
| 4,719,917 A | 1/1988 | Barrows et al. |
| 4,724,840 A | 2/1988 | McVay et al. |
| 4,728,020 A | 3/1988 | Green et al. |
| 4,741,337 A | 5/1988 | Smith et al. |
| 4,752,024 A | 6/1988 | Green et al. |
| 4,753,636 A | 6/1988 | Free |
| 4,762,260 A | 8/1988 | Richards et al. |
| 4,776,506 A | 10/1988 | Green |
| 4,789,090 A | 12/1988 | Blake, III |
| 4,799,483 A | 1/1989 | Kraff |
| 4,802,478 A | 2/1989 | Powell |
| 4,809,695 A | 3/1989 | Gwathmey et al. |
| 4,867,083 A | 9/1989 | Fietta et al. |
| 4,869,414 A | 9/1989 | Green et al. |
| 4,873,976 A | 10/1989 | Schreiber |
| 4,887,601 A | 12/1989 | Richards |
| 4,887,756 A | 12/1989 | Puchy |
| 4,895,148 A | 1/1990 | Bays et al. |
| 4,899,745 A | 2/1990 | Laboreau et al. |
| 4,915,100 A | 4/1990 | Green |
| 4,924,866 A | 5/1990 | Yoon |
| 4,932,960 A | 6/1990 | Green et al. |
| 4,938,408 A | 7/1990 | Bedi et al. |
| 4,950,281 A | 8/1990 | Kirsch et al. |
| 4,955,898 A | 9/1990 | Matsutani et al. |
| 4,969,300 A | 11/1990 | Pope |
| 4,969,591 A | 11/1990 | Richards et al. |
| 4,976,715 A | 11/1990 | Bays et al. |
| 4,976,686 A | 12/1990 | Ball et al. |
| 4,979,954 A | 12/1990 | Gwathmey et al. |
| 4,981,149 A | 1/1991 | Yoon et al. |
| 4,994,073 A | 2/1991 | Green |
| 5,002,562 A | 3/1991 | Oberlander |
| 5,002,563 A | 3/1991 | Pyka |
| 5,007,921 A | 4/1991 | Brown |
| 5,015,252 A | 5/1991 | Jones |
| 5,026,390 A | 6/1991 | Brown |
| 5,035,692 A | 7/1991 | Lyon et al. |
| 5,041,128 A | 8/1991 | Korthoff |
| 5,044,540 A | 9/1991 | Dulebohn |
| 5,047,047 A | 9/1991 | Yoon |
| 5,053,047 A | 10/1991 | Yoon |
| 5,058,315 A | 10/1991 | Wagner |
| 5,062,563 A | 11/1991 | Green et al. |
| 5,067,959 A | 11/1991 | Korthoff |
| 5,078,731 A | 1/1992 | Hayhurst |
| 5,080,665 A | 1/1992 | Jarrett et al. |
| 5,084,063 A | 1/1992 | Korthoff |
| 5,089,009 A | 2/1992 | Green |
| 5,089,010 A | 2/1992 | Korthoff |
| 5,089,011 A | 2/1992 | Korthoff |
| 5,104,394 A | 4/1992 | Green et al. |
| 5,108,422 A | 4/1992 | Green et al. |

(56) References Cited

U.S. PATENT DOCUMENTS

| | | |
|---|---|---|
| 5,123,913 A | 6/1992 | Wilk et al. |
| 5,129,570 A | 7/1992 | Schulze et al. |
| 5,133,738 A | 7/1992 | Korthoff et al. |
| 5,139,514 A | 8/1992 | Korthoff et al. |
| 5,156,315 A | 10/1992 | Green et al. |
| 5,156,609 A | 10/1992 | Nakao et al. |
| 5,156,615 A | 10/1992 | Korthoff et al. |
| 5,158,566 A | 10/1992 | Painetti |
| 5,158,567 A | 10/1992 | Green |
| 5,160,339 A | 11/1992 | Chen et al. |
| 5,176,306 A | 1/1993 | Heimerl et al. |
| 5,179,964 A | 1/1993 | Cook |
| 5,211,644 A | 5/1993 | VanBeek et al. |
| 5,211,722 A | 5/1993 | Wagner |
| 5,222,976 A | 6/1993 | Yoon |
| 5,226,912 A | 7/1993 | Kaplan et al. |
| 5,236,440 A | 8/1993 | Hlavacek |
| 5,242,457 A | 9/1993 | Akopov et al. |
| 5,257,713 A | 11/1993 | Green et al. |
| 5,258,009 A | 11/1993 | Conners |
| 5,258,010 A | 11/1993 | Green et al. |
| 5,258,012 A | 11/1993 | Luscombe et al. |
| 5,259,845 A | 11/1993 | Korthoff |
| 5,263,973 A | 11/1993 | Cook |
| 5,269,783 A | 12/1993 | Sander |
| 5,269,792 A | 12/1993 | Kovac et al. |
| 5,275,166 A | 1/1994 | Vaitekunas et al. |
| 5,282,807 A | 2/1994 | Knoepfler |
| 5,285,944 A | 2/1994 | Green et al. |
| 5,292,326 A | 3/1994 | Green et al. |
| 5,293,881 A | 3/1994 | Green et al. |
| 5,297,714 A | 3/1994 | Kramer |
| 5,304,204 A | 4/1994 | Bregen |
| 5,306,281 A | 4/1994 | Beurrier |
| 5,324,307 A | 6/1994 | Jarrett et al. |
| 5,330,503 A | 7/1994 | Yoon |
| 5,333,772 A | 8/1994 | Rothfuss et al. |
| 5,337,937 A | 8/1994 | Remiszewski et al. |
| 5,342,376 A | 8/1994 | Ruff |
| 5,350,400 A | 9/1994 | Esposito et al. |
| 5,356,424 A | 10/1994 | Buzerak et al. |
| 5,364,003 A | 11/1994 | Williamson, IV |
| 5,366,134 A | 11/1994 | Green et al. |
| 5,389,102 A | 2/1995 | Green et al. |
| 5,392,979 A | 2/1995 | Green et al. |
| 5,398,861 A | 3/1995 | Green |
| D357,316 S | 4/1995 | Green et al. |
| 5,413,584 A | 5/1995 | Schulze |
| 5,415,334 A | 5/1995 | Williamson, IV et al. |
| 5,417,361 A | 5/1995 | Williamson, IV |
| 5,423,856 A | 6/1995 | Green |
| 5,423,857 A | 6/1995 | Rosenman et al. |
| 5,425,489 A | 6/1995 | Shichman et al. |
| 5,425,747 A | 6/1995 | Brotz |
| 5,456,400 A | 10/1995 | Shichman et al. |
| 5,456,401 A | 10/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,489,058 A | 2/1996 | Plyley et al. |
| 5,489,287 A | 2/1996 | Green et al. |
| 5,499,990 A | 3/1996 | Schulken et al. |
| 5,505,363 A | 4/1996 | Green et al. |
| 5,509,596 A | 4/1996 | Green et al. |
| 5,514,149 A | 5/1996 | Green et al. |
| 5,515,797 A | 5/1996 | Janouschek et al. |
| 5,542,594 A | 8/1996 | McKean et al. |
| 5,544,802 A | 8/1996 | Crainich |
| 5,549,619 A | 8/1996 | Peters et al. |
| 5,551,622 A | 9/1996 | Yoon |
| 5,558,266 A | 9/1996 | Green et al. |
| 5,562,241 A | 10/1996 | Knodel et al. |
| 5,571,285 A | 11/1996 | Chow et al. |
| 5,573,541 A | 11/1996 | Green et al. |
| 5,573,542 A | 11/1996 | Stevens |
| 5,575,800 A | 11/1996 | Gordon |
| 5,579,978 A | 12/1996 | Green et al. |
| 5,584,859 A | 12/1996 | Brotz |
| 5,591,178 A | 1/1997 | Green et al. |
| 5,593,423 A | 1/1997 | Person et al. |
| 5,615,816 A | 4/1997 | Deschenes et al. |
| 5,618,311 A | 4/1997 | Gryskiewicz |
| 5,641,234 A | 6/1997 | Blumberg |
| 5,645,567 A | 7/1997 | Crainich |
| 5,655,698 A | 8/1997 | Yoon |
| 5,658,312 A | 8/1997 | Green et al. |
| 5,662,258 A | 9/1997 | Knodel et al. |
| 5,662,655 A | 9/1997 | Laboreau et al. |
| 5,667,527 A | 9/1997 | Cook |
| 5,706,997 A | 1/1998 | Green et al. |
| 5,722,981 A | 3/1998 | Stevens |
| 5,725,538 A | 3/1998 | Green et al. |
| 5,725,554 A | 3/1998 | Simon et al. |
| 5,728,108 A | 3/1998 | Griffiths et al. |
| 5,741,278 A | 4/1998 | Stevens |
| 5,782,844 A | 7/1998 | Yoon et al. |
| 5,792,152 A | 8/1998 | Klein et al. |
| 5,794,834 A | 8/1998 | Hamblin et al. |
| 5,816,471 A | 10/1998 | Plyley et al. |
| 5,829,662 A | 11/1998 | Allen et al. |
| 5,843,084 A | 12/1998 | Hart et al. |
| 5,871,135 A | 2/1999 | Williamson, IV et al. |
| 5,878,937 A | 3/1999 | Green et al. |
| 5,902,311 A | 5/1999 | Andreas et al. |
| 5,902,319 A | 5/1999 | Daley |
| 5,908,149 A | 6/1999 | Welch et al. |
| 5,908,427 A | 6/1999 | McKean et al. |
| 5,921,994 A | 7/1999 | Andreas et al. |
| 5,947,999 A | 9/1999 | Groiso |
| 5,964,774 A | 10/1999 | Mckean et al. |
| 5,976,160 A | 11/1999 | Crainich |
| 5,984,949 A | 11/1999 | Levin |
| 5,993,476 A | 11/1999 | Groiso |
| 6,036,699 A | 3/2000 | Andreas et al. |
| 6,036,701 A | 3/2000 | Rosenman et al. |
| 6,039,753 A | 3/2000 | Meislin |
| 6,045,560 A | 4/2000 | McKean et al. |
| 6,066,160 A | 5/2000 | Colvin et al. |
| 6,083,242 A | 7/2000 | Cook |
| 6,090,131 A | 7/2000 | Daley |
| 6,120,526 A | 9/2000 | Daley |
| 6,131,789 A | 10/2000 | Schulze et al. |
| 6,136,010 A | 10/2000 | Modesitt et al. |
| 6,149,658 A | 11/2000 | Gardiner et al. |
| 6,152,934 A | 11/2000 | Harper et al. |
| 6,159,224 A | 12/2000 | Yoon |
| 6,179,840 B1 | 1/2001 | Bowman |
| 6,200,330 B1 | 3/2001 | Benderev et al. |
| 6,241,747 B1 | 6/2001 | Ruff |
| 6,250,532 B1 | 6/2001 | Green et al. |
| 6,270,517 B1 | 8/2001 | Brotz |
| 6,293,961 B2 | 9/2001 | Schwartz et al. |
| 6,325,007 B1 | 12/2001 | Farmer |
| 6,325,805 B1 | 12/2001 | Ogilvie et al. |
| 6,387,104 B1 | 5/2002 | Pugsley et al. |
| 6,387,113 B1 | 5/2002 | Hawkins et al. |
| 6,409,743 B1 | 6/2002 | Fenton, Jr. |
| 6,423,073 B2 | 7/2002 | Bowman |
| 6,423,088 B1 | 7/2002 | Fenton, Jr. |
| 6,425,903 B1 | 7/2002 | Voegele |
| 6,443,962 B1 | 9/2002 | Gaber |
| 6,485,504 B1 | 11/2002 | Johnson et al. |
| 6,514,263 B1 | 2/2003 | Stefanchik et al. |
| 6,530,933 B1 | 3/2003 | Leung et al. |
| 6,554,852 B1 | 4/2003 | Oberlander |
| 6,599,310 B2 | 7/2003 | Leung et al. |
| 6,601,748 B1 | 8/2003 | Fung |
| 6,610,079 B1 | 8/2003 | Li et al. |
| 6,619,529 B2 | 9/2003 | Green et al. |
| 6,626,916 B1 | 9/2003 | Yeung et al. |
| 6,629,988 B2 | 10/2003 | Weadock |
| 6,638,297 B1 | 10/2003 | Huiterna |
| 6,652,538 B2 | 11/2003 | Kayan et al. |

(56) References Cited

U.S. PATENT DOCUMENTS

| | | |
|---|---|---|
| 6,652,563 B2 | 11/2003 | Dreyfuss |
| 6,666,872 B2 | 12/2003 | Barreiro et al. |
| 6,692,499 B2 | 2/2004 | Tormala et al. |
| 6,715,654 B2 | 4/2004 | Sugihara et al. |
| 6,726,695 B2 | 4/2004 | Tong |
| 6,726,705 B2 | 4/2004 | Peterson |
| 6,733,506 B1 | 5/2004 | McDevitt et al. |
| 6,767,356 B2 | 7/2004 | Kanner et al. |
| 6,773,437 B2 | 8/2004 | Ogilvie et al. |
| 6,989,017 B2 | 1/2006 | Howell et al. |
| 7,008,435 B2 | 3/2006 | Cummins |
| 7,048,171 B2 | 5/2006 | Thornton et al. |
| 7,056,331 B2 | 6/2006 | Kaplan et al. |
| 7,104,999 B2 | 9/2006 | Overaker |
| 7,112,214 B2 | 9/2006 | Peterson |
| 7,118,581 B2 | 10/2006 | Friden |
| D532,107 S | 11/2006 | Peterson |
| 7,238,195 B2 | 7/2007 | Viola |
| 7,547,315 B2 | 6/2009 | Peterson et al. |
| 7,618,441 B2 | 11/2009 | Groiso |
| 7,682,372 B2 | 3/2010 | Peterson |
| 7,686,200 B2 | 3/2010 | Peterson |
| D635,259 S | 3/2011 | Peterson et al. |
| 7,942,301 B2 | 5/2011 | Sater |
| 7,950,559 B2 | 5/2011 | Peterson et al. |
| 8,016,867 B2 | 9/2011 | Bowman |
| 8,066,736 B2 | 11/2011 | Peterson et al. |
| 8,074,857 B2 | 12/2011 | Peterson et al. |
| 8,100,939 B2 | 1/2012 | Peterson |
| 8,105,342 B2 | 1/2012 | Onuki et al. |
| 8,277,481 B2 | 10/2012 | Kawaura et al. |
| 8,337,523 B2 | 12/2012 | Baker et al. |
| 8,506,591 B2 | 8/2013 | Danielson et al. |
| 8,518,055 B1 | 8/2013 | Cardinale et al. |
| 8,821,517 B2 | 9/2014 | Peterson et al. |
| 8,894,669 B2 | 11/2014 | Nering et al. |
| 8,920,439 B2 | 12/2014 | Cardinale et al. |
| 8,961,540 B2 | 2/2015 | Baker et al. |
| 9,055,945 B2 | 6/2015 | Miksza et al. |
| 9,119,629 B2 | 9/2015 | Cardinale et al. |
| D744,646 S | 12/2015 | Nering et al. |
| 9,232,943 B2 | 1/2016 | Rogers et al. |
| D752,219 S | 3/2016 | Peterson et al. |
| 9,364,228 B2 | 6/2016 | Straehnz et al. |
| 9,498,211 B2 | 11/2016 | Cohn et al. |
| 9,539,005 B2 | 1/2017 | Gupta et al. |
| 9,713,472 B2 | 7/2017 | Peterson et al. |
| 9,844,377 B2 * | 12/2017 | Peterson .............. A61B 17/10 |
| 9,855,041 B2 | 1/2018 | Nering et al. |
| 10,004,499 B2 | 6/2018 | Cardinale et al. |
| 10,045,777 B2 | 8/2018 | Rogers et al. |
| 10,085,747 B2 * | 10/2018 | Peterson ............ A61B 17/0682 |
| 10,492,782 B2 | 12/2019 | Peterson et al. |
| 11,045,195 B2 * | 6/2021 | Peterson .............. A61B 17/10 |
| 11,419,607 B2 | 8/2022 | Peterson et al. |
| 2001/0027322 A1 | 10/2001 | Bowman |
| 2002/0007184 A1 | 1/2002 | Ogilvie et al. |
| 2002/0019636 A1 | 2/2002 | Ogilvie et al. |
| 2002/0111641 A1 | 8/2002 | Peterson et al. |
| 2002/0133181 A1 | 9/2002 | Tong |
| 2003/0009193 A1 | 1/2003 | Corsaro |
| 2003/0028218 A1 | 2/2003 | Bauer |
| 2003/0071406 A1 | 4/2003 | Sellers |
| 2003/0139746 A1 | 7/2003 | Groiso |
| 2003/0167072 A1 | 9/2003 | Oberlander |
| 2003/0233108 A1 | 12/2003 | Gellman et al. |
| 2003/0236550 A1 | 12/2003 | Peterson |
| 2003/0236551 A1 | 12/2003 | Peterson |
| 2004/0059377 A1 | 3/2004 | Peterson |
| 2004/0059378 A1 | 3/2004 | Peterson et al. |
| 2005/0033317 A1 | 2/2005 | Ables |
| 2005/0085857 A1 | 4/2005 | Peterson |
| 2005/0116008 A1 | 6/2005 | Thornton et al. |
| 2005/0149064 A1 | 7/2005 | Peterson et al. |
| 2005/0182444 A1 | 8/2005 | Peterson |
| 2005/0288689 A1 | 12/2005 | Kammerer et al. |
| 2006/0009792 A1 | 1/2006 | Baker et al. |
| 2006/0011693 A1 | 1/2006 | Wywialowski et al. |
| 2006/0097027 A1 | 5/2006 | Brown |
| 2006/0122635 A1 | 6/2006 | Naegeli et al. |
| 2006/0135988 A1 | 6/2006 | Peterson |
| 2006/0253131 A1 | 11/2006 | Wolniewicz |
| 2007/0049969 A1 | 3/2007 | Peterson |
| 2007/0185504 A1 | 8/2007 | Manetakis et al. |
| 2007/0232954 A1 | 10/2007 | Harris et al. |
| 2008/0249563 A1 | 10/2008 | Peterson et al. |
| 2009/0093824 A1 | 4/2009 | Hasan et al. |
| 2009/0206127 A1 | 8/2009 | Danielson et al. |
| 2010/0292715 A1 | 11/2010 | Nering et al. |
| 2012/0083831 A1 | 4/2012 | Peterson |
| 2012/0145765 A1 | 6/2012 | Peterson et al. |
| 2012/0325889 A1 | 12/2012 | Danielson et al. |
| 2013/0267997 A1 | 10/2013 | Peterson et al. |
| 2015/0112369 A1 | 4/2015 | Peterson et al. |
| 2015/0127046 A1 | 5/2015 | Peterson |
| 2015/0133966 A1 | 5/2015 | Gupta et al. |
| 2015/0305740 A1 | 10/2015 | Peterson et al. |
| 2016/0242772 A1 | 8/2016 | Peterson et al. |
| 2017/0071602 A1 | 3/2017 | Peterson et al. |
| 2018/0125493 A1 | 5/2018 | Peterson et al. |
| 2021/0267598 A1 * | 9/2021 | Peterson .............. A61B 17/064 |

FOREIGN PATENT DOCUMENTS

| | | | |
|---|---|---|---|
| EP | 1 531 736 | 5/2005 | |
| FR | 2549544 | 1/1985 | ............. F16B 15/00 |
| JP | 04-226642 | 8/1992 | ........... A61B 17/068 |
| JP | 05-504892 | 7/1993 | |
| JP | 06233772 | 8/1994 | ............. A61B 17/04 |
| JP | 7-124166 | 5/1995 | ........... A61B 17/068 |
| JP | 2000-217829 | 8/2000 | ........... A61B 17/068 |
| JP | 2000-517197 | 12/2000 | |
| JP | 2005-530563 | 10/2005 | ........... A61B 17/068 |
| JP | 2005-530567 | 10/2005 | ............. A61B 17/06 |
| WO | WO 97/18761 | 5/1997 | ............. A61B 17/08 |
| WO | WO 00/57796 | 10/2000 | ........... A61B 17/064 |
| WO | WO 00/67644 | 11/2000 | ........... A61B 17/068 |
| WO | WO 2004/000105 | 12/2003 | |
| WO | WO 2010/141872 | 12/2010 | ............. A61B 17/04 |

OTHER PUBLICATIONS

Brochure: La Sutura Perde il Filo, Farmitalia Carlo Erba, 4 pgs., not dated.

Evaluation of New Absorbable Lactomer Subcuticular Staple, G.C. Zachmann, P.A. Foresman, T.J. Bill, D.J. Bentrem, G.T. Rodeheaver, R.F. Edlich, Journal of Applied Biomaterial, vol. 5, No. 3, pp. 221-116, 1994.

Suturtek Incorporated, http://www.suturtek.com/productInfo/, Jan. 31, 2007, p. 1 of 1, North Chelmsford, Massachusetts.

Petition for Inter Partes Review of U.S. Pat. No. 8,821,517 filed with the United States Patent and Trademark office Before the Patent Trial and Appeal Board on May 15, 2017.

Exhibit No. 1001—U.S. Pat. No. 8,821,517 ('517 Patent) (Filed on May 15, 2017).

Exhibit No. 1002—Declaration of Charles Rogers, Phd (Filed on May 15, 2017).

Exhibit No. 1003—U.S. Publication 2012/0325889 ('889 Publication) (Filed on May 15, 2017).

Exhibit No. 1004—Claims From U.S. Appl. No. 13/796,798 ('798 Application) (filed May 15, 2017).

Exhibit No. 1005—Excerpt From '517 Patent File History (Filed on May 15, 2017).

Exhibit No. 1006—U.S. Pat. No. 5,489,287 ('287 Patent or Green) (Filed on May 15, 2017).

Exhibit No. 1007A, B—Photos of Petitioner's Stapler (Filed on May 15, 2017).

Exhibit No. 1008—Excerpt From '200 Patent File History (Filed on May 15, 2017).

Exhibit No. 1009—Letter from Patent Owner to Petitioner (Filed on May 15, 2017).

(56) References Cited

OTHER PUBLICATIONS

Exhibit No. 1010—Photo of Commercial Patent Owner's Commercial Stapler (Filed on May 15, 2017).
Exhibit No. 1011—Photo of Commercial Patent Owner's Commercial Stapler (Filed on May 15, 2017).
Exhibit No. 1012—Declaration of Peter Stokes (Filed on May 15, 2017).
Exhibit No. 1013—Principles of Wound Management (Filed on May 15, 2017).
Exhibit No. 1014—Pediatric Emergency Procedures (Filed on May 15, 2017).
Exhibit No. 1015—Ethicon Wound Closure Manual (Filed on May 15, 2017).
Exhibit No. 1016—U.S. Pat. No. 3,716,058 (Filed on May 15, 2017).
Exhibit No. 1017—Declaration of H. V. Mendenhall, DVM, Phd (Filed on May 15, 2017).
Exhibit No. 1018—Excerpt from '838 Application (Filed on May 15, 2017).

\* cited by examiner

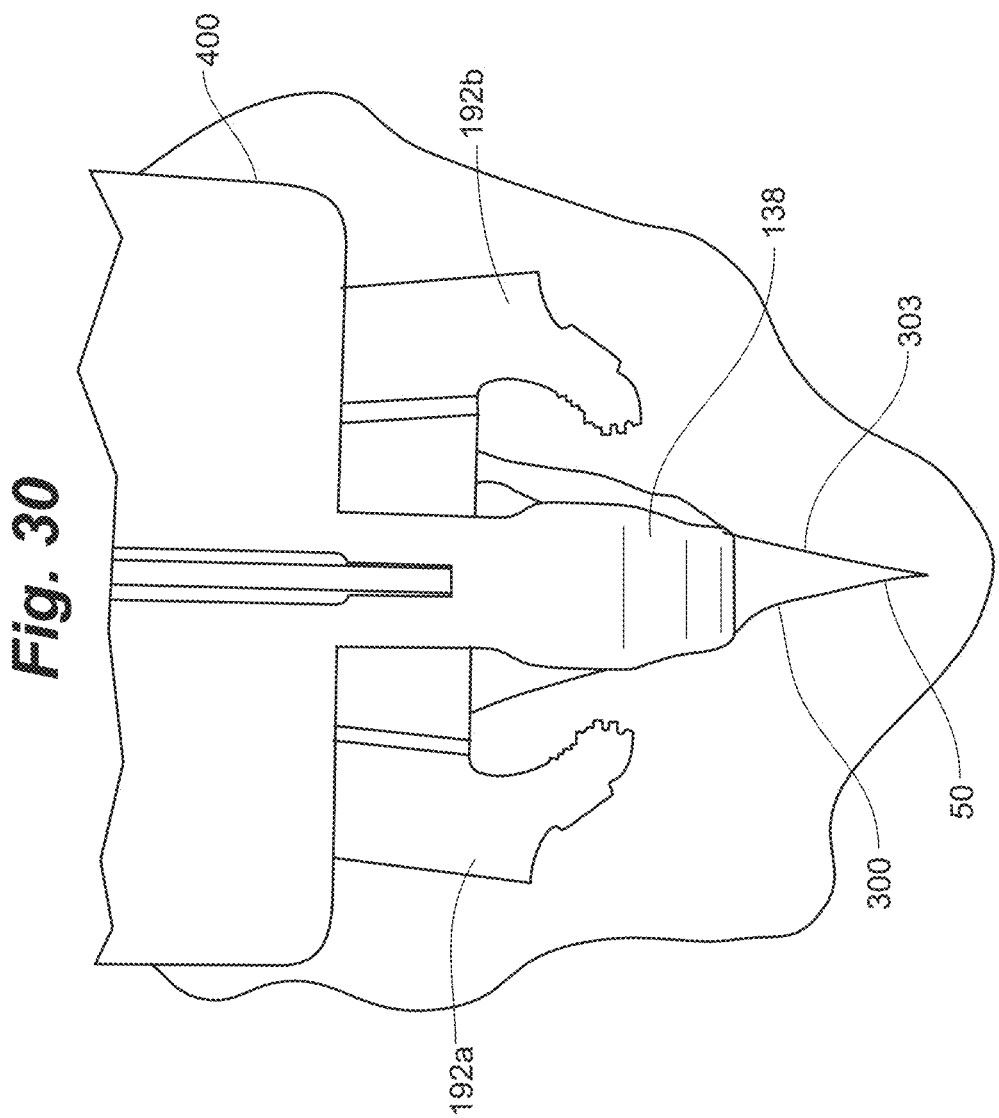

METHOD AND APPARATUS FOR WOUND CLOSURE WITH SEQUENTIAL TISSUE POSITIONING AND RETENTION

RELATED APPLICATION

This application is a division of and claims priority under 35 U.S.C. § 120 to U.S. application Ser. No. 15/843,361, filed on Dec. 15, 2017, which is a continuation of U.S. application Ser. No. 14/262,071, filed on Apr. 25, 2014, now U.S. Pat. No. 9,844,377. The entire contents of each of these priority applications are incorporated herein by reference.

FIELD OF THE INVENTION

The present invention is generally directed to the field of wound closure. More specifically, the present invention is directed to an apparatus and related methods of use for grasping, positioning and retaining opposed sides of a tissue wound for securing with a tissue fastener.

BACKGROUND OF THE INVENTION

Throughout history, sutures have been utilized to capture and retain tissue in approximation during a wound healing period. More recently, medical staplers and staples have been developed to speed the closure process. While conventional sutures and medical staplers can be very effective, they are each prone to infection, unsightly scarring and can require subsequent medical follow ups for removal of the suture or staple by a medical professional.

In a desire to improve upon the existing techniques for wound closure, an approach to wound closure through the insertion of a bioabsorbable fastener is described in U.S. Pat. Nos. 6,726,705, 7,112,214, 7,547,315, 7,686,200, 7,950,559, 8,066,736 and 8,074,857 and US Patent Publications 2012/0145765 and 2013/0267997 to Peterson et al., all of which are herein incorporated by reference in their entirety. These devices and methods have been commercialized as the INSORB® available from Incisive Surgical, Inc. of Plymouth, MN. By using a dermal insertion and fastening approach as taught by Peterson et al., visible scarring is minimized and incidences of infection are significantly reduced.

In order to successfully implement the dermal insertion techniques and methods taught by Peterson et al., it is especially important that tissue on opposed sides of a wound be properly positioned and retained during introduction of a fastener. As such, it would be advantageous to further improve upon the devices and methods as taught by Peterson et al. so as to further assist medical professionals in properly grasping and positioning tissue for presentation to a bioabsorbable fastener.

SUMMARY OF THE INVENTION

Apparatus and related methods for sequentially positioning and retaining opposing sides of a tissue wound. The apparatus includes a device body having a head portion for positioning between first and second sides of the wound, with the head portion defining first and second retention zones on opposed side of the head portion. The device body further includes first and second approximation arms. The device body further includes an actuation assembly defining four operational positions including a first ready state and three stages of operation for delivery of a fastener. In a first ready state, the head portion can be placed into a wound and against a first side of tissue. In a first stage of operation, the first approximation arm is positioned proximate the first retention zone of the head portion such that the first side of tissue is retained and positioned with respect to the head portion. In a second stage of operation, the second approximation arm is positioned proximate the second retention zone of the head portion such that the second side of tissue is retained and positioned on an opposite side of the head portion from the first side of tissue. In a third stage of operation, a penetrator assembly is advanced such that a pair of penetrators advance through the first and second retention zones to advance a fastener into the first and second sides of tissue that are retained and positioned with respect to the head portion. The apparatus can be returned to the ready state, wherein the previously delivered fastener retains the first and second sides of tissue in approximation and the method can be repeated along the wound for delivery of additional fasteners from the device body.

A first aspect of the present invention can include representative methods for securing skin tissue with a fastener involving sequential positioning and retention of skin tissue on opposing sides of a wound. The method can comprise positioning a head portion of a fastening device within the skin wound. The method can further comprise positioning a first side of skin tissue between a first approximation arm of the fastening device and the head portion. The method can further comprise retaining the first side of skin tissue between the first approximation arm and the head portion. While the first side of skin tissue remains retained between the first approximation arm and the head portion, the method can further comprise positioning a second side of skin tissue between a second approximation arm and the head portion. The method can further comprise retaining the second side of skin tissue between the second approximation arm and the head portion. Finally, the method can comprise delivering a fastener into the retained first and second sides of skin tissue. In some embodiments, the steps of positioning the first and second sides of skin tissue can involve sequentially grasping and placing the first side skin tissue in proximity to the head portion using a conventional forceps followed by sequentially grasping and placing the second side of skin tissue in proximity to the head portion. In some embodiments, the step of delivering the fastener can include inserting a staple arm into each for the first and second sides of skin tissue such that a backspan resides across a vertical interface defined between the first and second sides of skin tissue. In some embodiments, the method of retaining the first and second sides of skin tissue can include advancing an actuator body on the fastening device such that the actuator body directs sequential, rotatable operation of the first and second actuation arms. In some embodiments, the method can further comprise directing penetrators into the retained first and second sides of skin tissue such that staple arms on the fastener can be deployed into pierced openings in the first and second sides of skin tissue.

In another aspect of the present invention, a skin fastening device can comprise a device body having a head portion, first and second approximation arms and an actuator body wherein manipulation of the actuator body results in sequential operation of the first and second approximation arms relative to the head portion. In a first stage of operation, the actuator body causes the first approximation arm to be manipulated into proximity with the head portion to define a first retention position for retaining a first side of skin tissue. In a second stage of operation, the actuator body causes the second approximation arm to be manipulated into proximity with the head portion to define a second retention position for retaining a second side of skin tissue. In a third stage of operation, the actuator body causes a fastener to be advanced toward the head portion for delivery of the fastener into the retained first and second sides of skin tissue. In one representative embodiment, the first and second approximation arms are rotatably coupled to the device body such that the first and second approximation arms are sequentially, rotatably manipulated into proximity with the head portion. In some embodiments, the first and second approximation arms and the actuator body are manipulated and along a shared planed defined by the device body. In another representative embodiment, the device body further comprises a penetrator assembly that is manipulated by the actuator body to advance the fastener toward the head portion. In some embodiments, the actuator body comprises first and second actuator surfaces that sequentially engage the first and second approximation arms. In some embodiments, the first and second approximation arms can each include a rotatable engagement member that engages the actuator body.

In another aspect of the present invention, the disclosed apparatus and methods involving sequential placement and retention of opposed sides of skin wounds can be utilized to close skin wounds, wherein the opposed sides can be difficult to approximate and/or retain. For instance, high tension wounds based on small wound sizes, such as, for example, laparoscopic skin ports or based on various locations of a body. In addition, the disclosed apparatus and methods can be especially beneficial in closing wounds resulting from tissue excision or irregular incisions or lacerations.

In yet another aspect of the present invention, a skin fastening device of the present invention can be fabricated to increase visibility and use of device allowing for operation by a single medical professional. In some embodiments, a head portion and first and second approximation arms can be constructed to have low profiles so as to not obstruct a user's view of a skin wound, the head portion or the approximation arms. In some embodiments, the first and second approximation arms can operate along a same plane as an actuator body within a device body such that manipulation of the arms does not restrict and overhead view of a fastening end of the device.

In another aspect of the present invention, a skin fastening device of the present invention can be fabricated of suitable materials for enhancing operation during closing of high tension skin wounds. In one representative embodiment, first and second approximation arms can be fabricated of a rigid, nonflexible material to as to promote consistent retention of skin tissue with respect to a head portion of the skin fastening device. In some embodiments, the first and second approximation arms can be fabricated from a medically compatible metal or metal alloy. In constructing the first and second approximation arms of a suitable rigid, nonflexible material, a profile of the first and second approximation arms can be reduced so as to enhance visibility of a fastening end of the device during use in wound closure.

In yet another aspect of the present invention, a skin fastening device of the present invention can be utilized in conjunction with one or more wound closure techniques for closing a full length of a skin wound. The skin fastening device of the present invention can have a reduced profile in a head portion and with first and second approximation arms such that the skin fastening device can be utilized at end regions of a longer wound that would be otherwise difficult to close with conventional techniques. For instance, the skin fastening device of the present invention can be utilized to deliver fasteners into end portions that are less than 2 cm in length. In addition, the skin fastening device of the present invention can be manipulated so as to delivery fasteners in horizontal, vertical or oblique orientations relative to an exterior surface of skin.

The above summary of the various representative embodiments of the invention is not intended to describe each illustrated embodiment or every implementation of the invention. Rather, the embodiments are chosen and described so that others skilled in the art can appreciate and understand the principles and practices of the invention.

BRIEF DESCRIPTION OF THE DRAWINGS

The invention can be more completely understood in consideration of the following detailed description of various embodiments of the invention in connection with the accompanying drawings, in which:

FIG. 30 is a top view of the skin opening of FIG. 25 following placement of the fastener of FIG. 13 in first and second tissue sides by the fastening device of FIG. 4 and with the fastening device of FIG. 4 being repositioned within the skin opening in a ready orientation.

Figure 1:
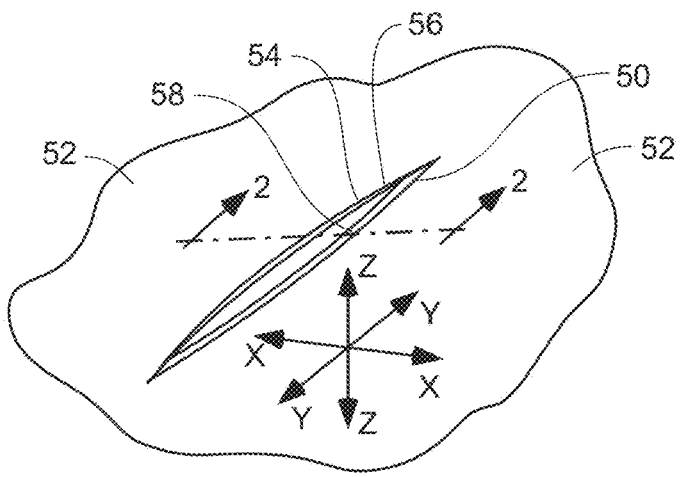
FIG. 1 is a top, perspective view of a skin tissue opening.

While the invention is amenable to various modifications and alternative forms, specifics thereof have been shown by way of example in the drawings and will be described in detail. It should be understood, however, that the intention is not to limit the invention to the particular embodiments as described. On the contrary, the intention is to cover all modifications, equivalents, and alternatives falling within the spirit and scope of the invention as defined by the appended claims.

DETAILED DESCRIPTION OF THE DRAWINGS

Figure 2:
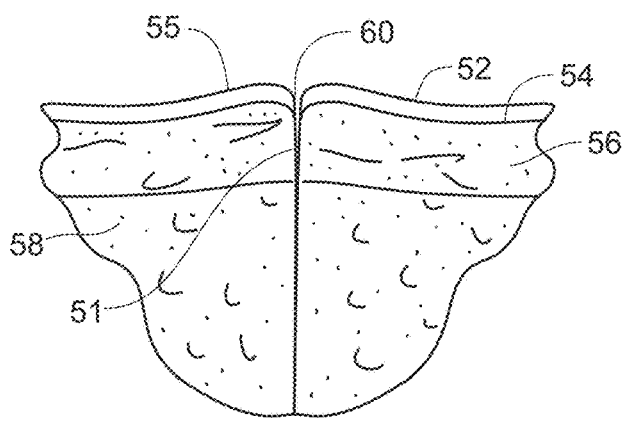
FIG. 2 is a section view of the skin tissue opening of FIG. 1 taken at line 2-2 of FIG. 1.
Figure 3:
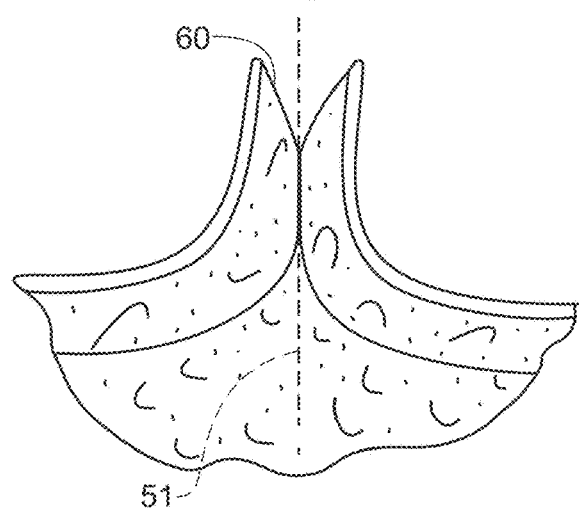
FIG. 3 is a section view of the skin tissue opening of FIG. 1 having opposing tissue sides arranged in an approximated, everted disposition.

In FIGS. 1-3 there is shown a depiction of a typical opening 50 in the surface of skin 52, such as may be made, for example, by a surgical incision or a wound. As illustrated in FIG. 1, for purposes of describing the present invention, opening 50 may be described as having a length or longitudinal orientation parallel to the y-y axis, a width orientation parallel to the x-x axis, and a depth orientation parallel to the z-z axis. The x-y-z axis for purposes of the present invention is defined with respect to an external tissue surface, which in the case of skin 52 is the outer surface. References to a vertical and horizontal planar orientation in connection with the present invention are made with respect to the external tissue surface at the site of the opening in question. The vertical inner surfaces 60 formed by each side of the opening 50 can be visualized as meeting along a generally vertical interface 51. It will be understood that in the case of an opening that extends over a curved tissue surface, the corresponding horizontal and vertical surfaces associated with the opening will be defined with respect to such curved tissue surface. It also will be understood that the vertical interface 51 may be vertical in only one orientation with respect to the tissue surface, such as in the case when an angled incision has formed the opening 50. Opening 50 can be under high tension based on its size or location on the body. For example, opening 50 can include laparoscopic skin ports or be the result of tissue excision or irregular incisions/lacerations.

As is best illustrated in the sectional views of FIGS. 2 and 3, human skin 52 generally has three discrete layers. These layers comprise an epidermal layer 54 of mostly non-living tissue having an exterior surface 55, a dermal layer 56 of mostly living tissue, and a subcutaneous tissue layer 58. Although the preferred embodiment of the present invention will be described with respect to human skin tissue 52, it will be understood that the present invention is applicable to closure of openings in other types of tissue having generally defined surfaces, such as fascia, membranes organs, vessels, vasculature, vascular pedicles, skin grafts, bladder and other biocompatible materials with generally defined surfaces such as artificial skin, artificial membranes and synthetic mesh.

It has long been known that the most rapid healing of a skin opening with a minimum of scarring occurs when the inner surfaces 60 of the living dermal layer 56 at each side of the vertical interface 51 of skin opening 50 are brought together and held in close contact in what is referred to as an everted position as is shown in exaggerated fashion in FIG. 3. To the extent that the primarily non-living material of epidermal layer 54 can be excluded from the healing opening, the rapidity and level of scar tissue formed during the healing process will be improved.

Figure 4:
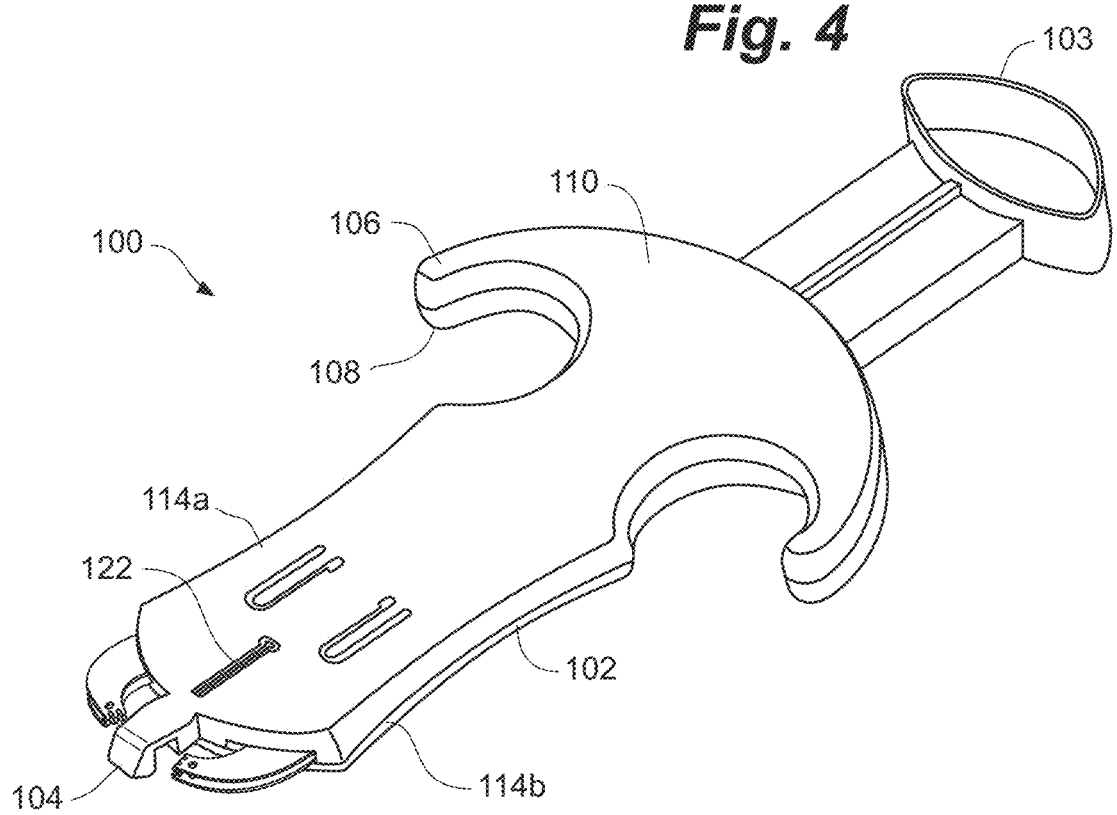
FIG. 4 is a top, perspective view of skin fastening device according to a representative embodiment of the present invention.
Figure 5:
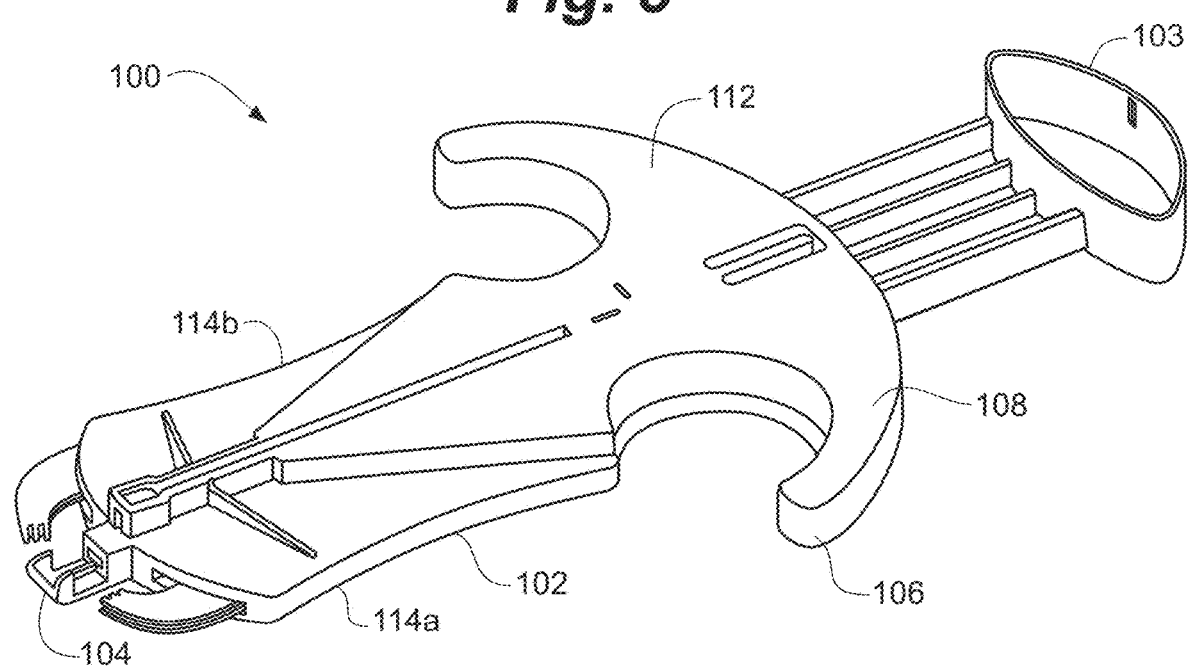
FIG. 5 is a bottom, perspective view of the skin fastening device of FIG. 4.

Referring now to FIGS. 4-5, a representative embodiment of a skin fastening device 100 for grasping and fastening skin tissue is illustrated. Generally, skin fastening device 100 and it various component parts as will be further described can be constructed of materials suitable for use in a surgical environment including metals such as, stainless steel or various polymers.

Generally, skin fastening device 100 comprises a device body 102 having an actuation end 103 and a fastening end 104. Device body 102 can comprise an upper housing member 106 and a lower housing member 108 that cooperatively define an upper body surface 110, a lower body surface 112 and pair of side surfaces 114a, 114b.

Figure 6:
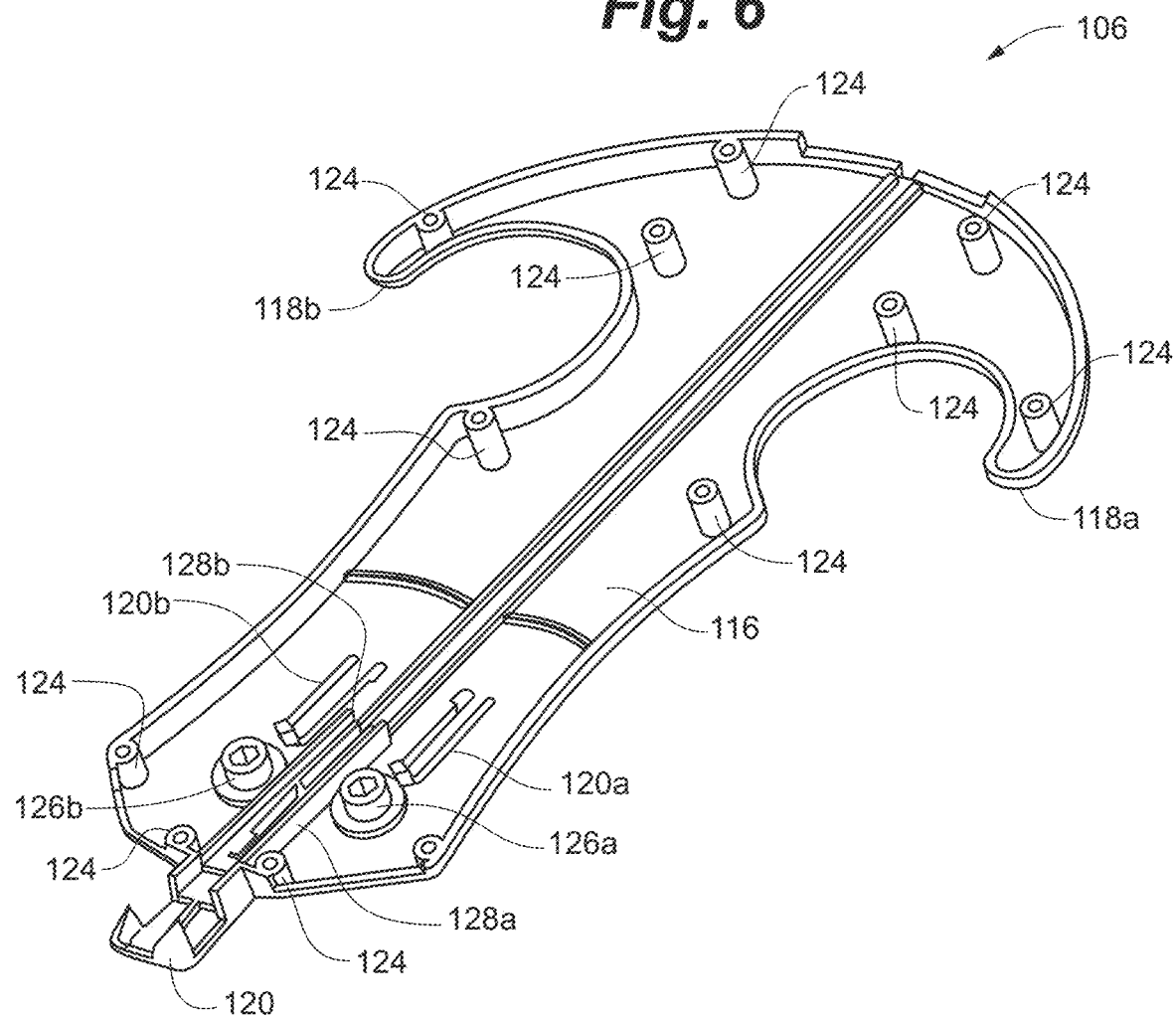
FIG. 6 is a bottom, perspective view of an upper housing member of the skin fastening device of FIG. 4.

Referring to FIGS. 4 and 6, upper housing member 106 generally defines the upper body surface 110, a downward facing surface 116, upper gripping members 118a, 118b and a head portion 120. Upper housing member can further comprise a pair of arm actuation windows 120a, 120b and a penetrator window 122, wherein all of these windows extend between the upper body surface 110 and downward facing surface 116. Downward facing surface 116 generally includes a plurality of female connector members 124, a pair of mounting projections 126a, 126b and a pair of parallel guide walls 128a, 128b.

Figure 7:
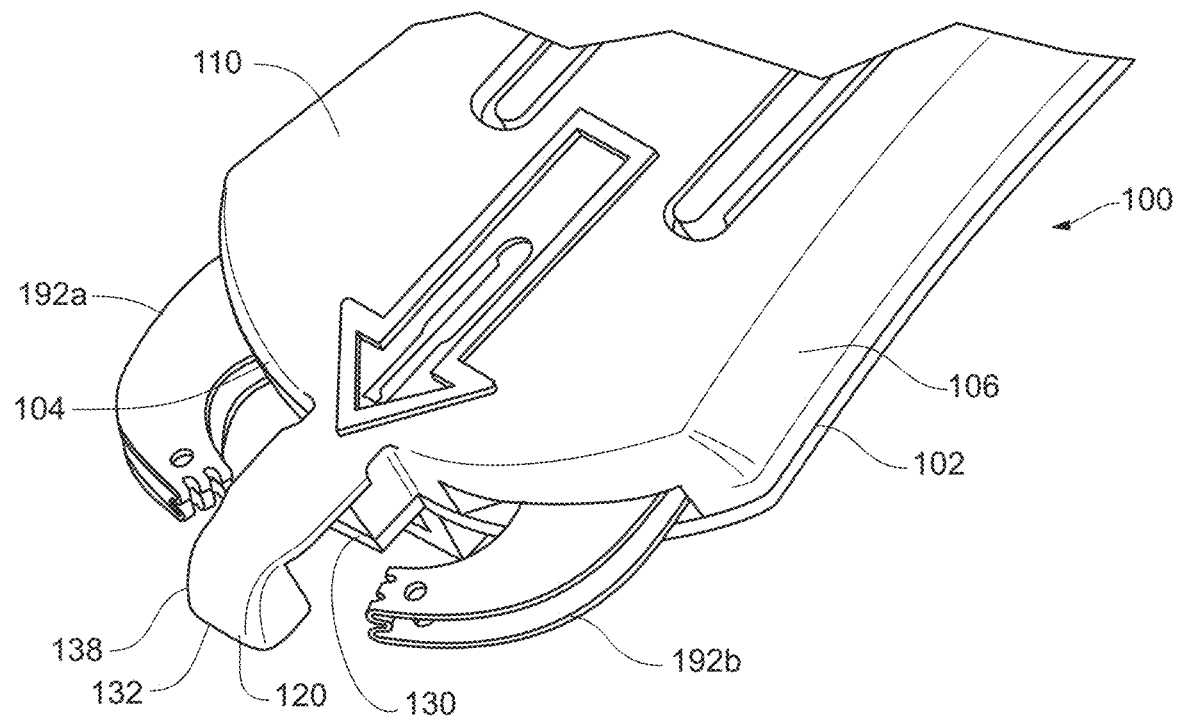
FIG. 7 is a top, detailed, perspective view of a fastening end of the skin fastening device of FIG. 4.
Figure 8:
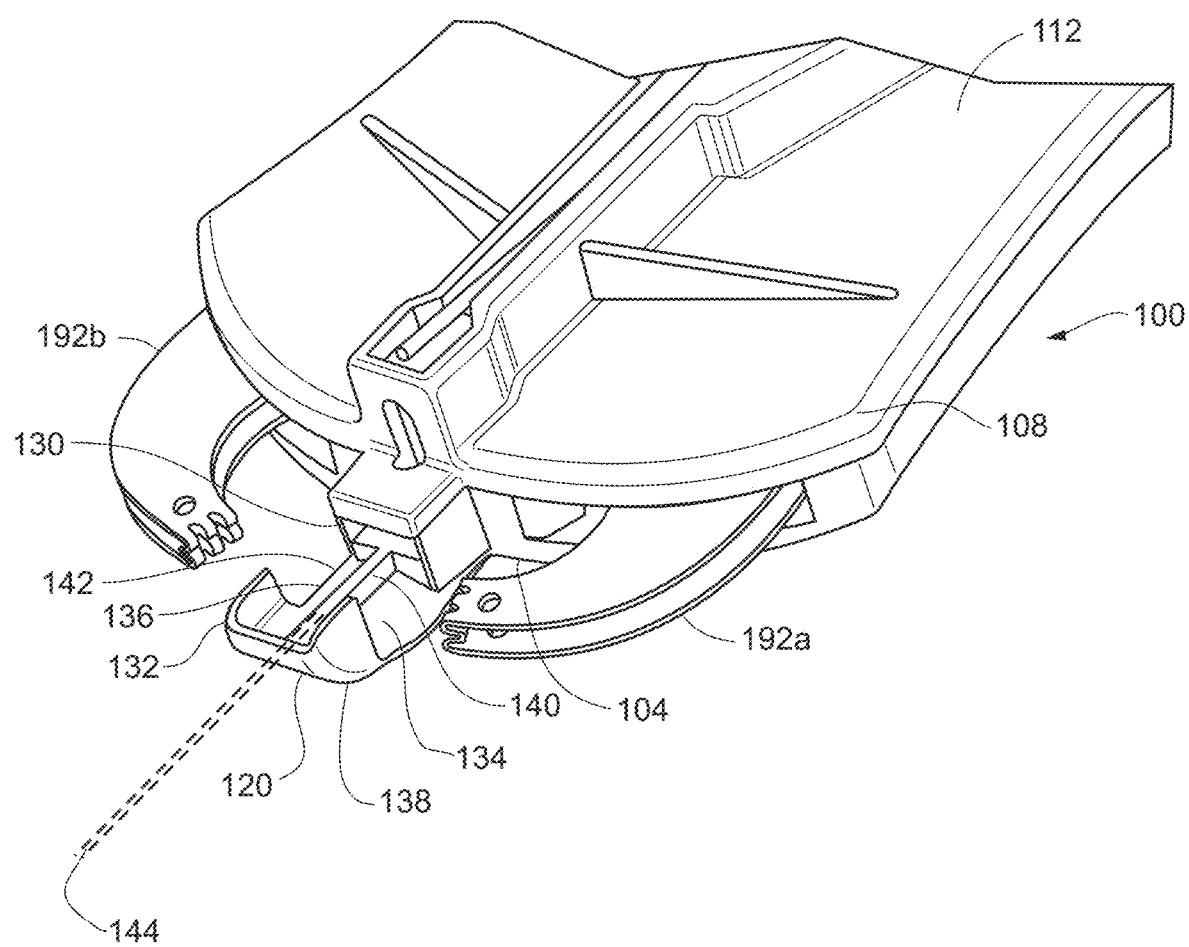
FIG. 8 is a bottom, detailed, perspective view of the fastening end of FIG. 7.

As seen in FIGS. 7 and 8, head portion 120 generally extends from the fastening end 104. Head portion 120 includes a proximal portion 130 and a distal portion 132. A pair of opposed retention zones, first retention zone 134 and second retention zone 136 are positioned on opposed sides of a head body 138. Both the first retention zone 134 and second retention zone 136 are defined by a respective retention surface 140, 142 that are separated by a retention distance 144.

Figure 9:
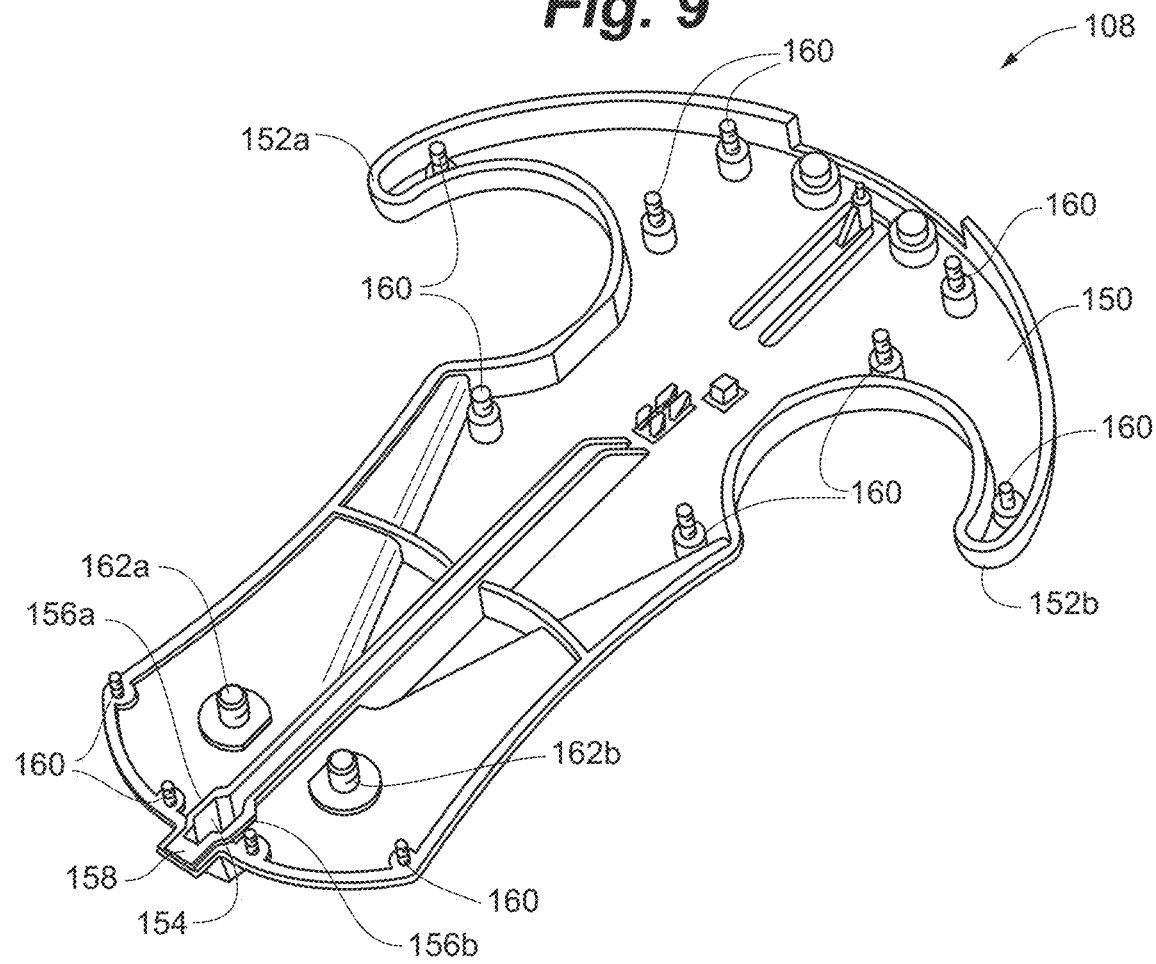
FIG. 9 is a top, perspective view of a lower housing member of the skin fastening device of FIG. 4.
Figure 10:
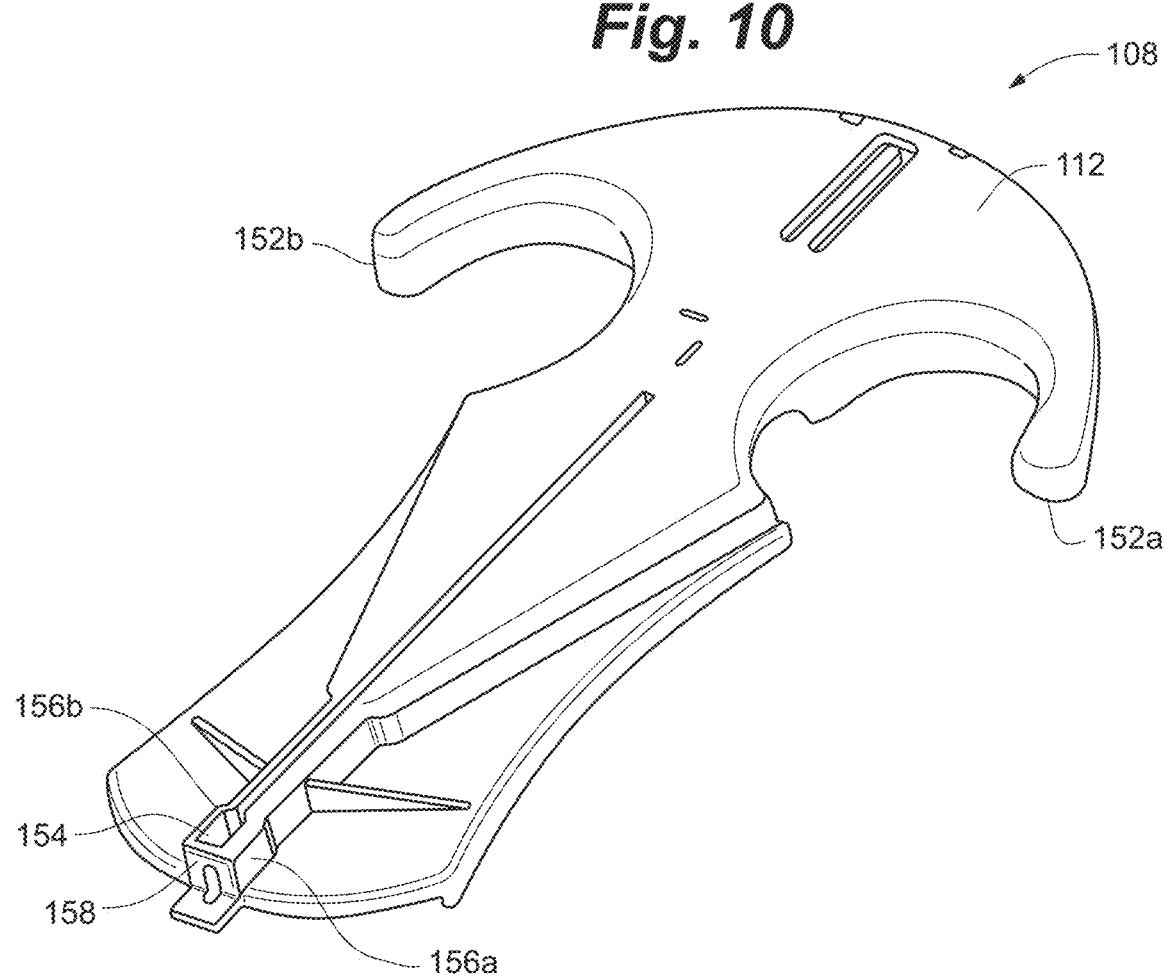
FIG. 10 is a bottom, perspective view of the lower housing member of FIG. 9.

Referring to FIGS. 5, 9 and 10, lower housing member 108 generally defines the lower body surface 112, an upward facing surface 150 and lower gripping members 152a, 152b. Lower housing member 108 includes a fastener stack aperture 154 extending between the lower body surface 112 and upward facing surface 150 that is defined by a pair of fastener stack side walls 156a, 156b and a fastener stack end wall 158. Upward facing surface 150 further comprises a plurality of male connector members 160 and a pair of mounting member 162a, 162b.

Figure 11:
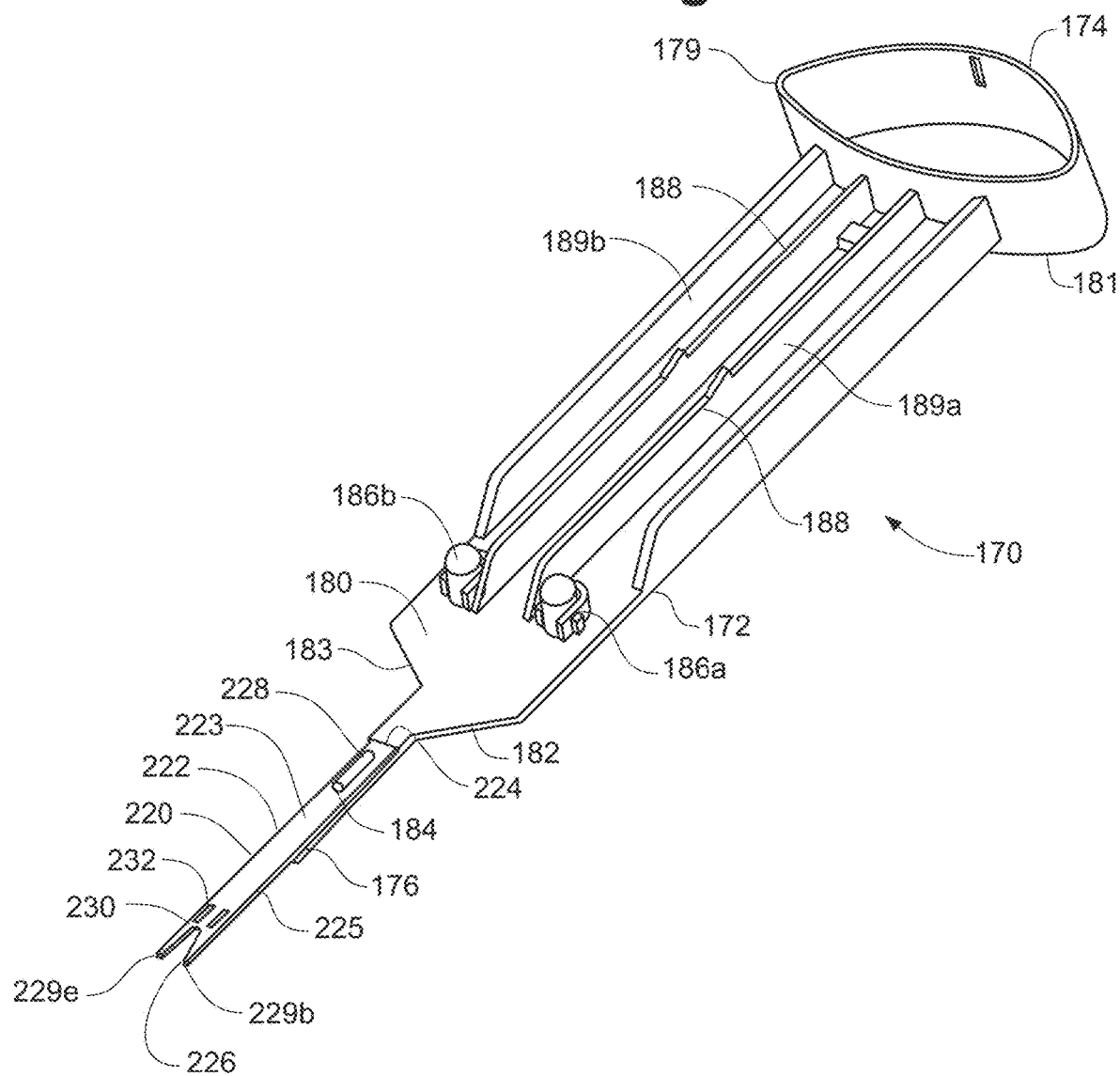
FIG. 11 is a top, perspective view of an actuator assembly including a penetrator assembly attached thereto for use in the skin fastening device of FIG. 4.

Referring now to FIG. 11, skin fastening device 100 further comprises an actuator assembly 170. Actuator assembly 170 generally includes an actuator body 172 having a grasping end 174, an actuation end 176, and upper actuator surface 178 and a lower actuator surface 180. The grasping end 174 can include a gripping feature 179 such as, for example, a handle portion 181. The actuation end 176 can comprise a first angled actuation surface 182, a second angled actuation surface 183 and an actuation projection 184. Actuator assembly can further comprise a pair of actuator projections 186a, 186b and a plurality of actuator walls 188 on the lower actuator surface 180. The plurality of actuator walls 188 defines a pair of actuator channels 189a, 189b.

Figure 12:
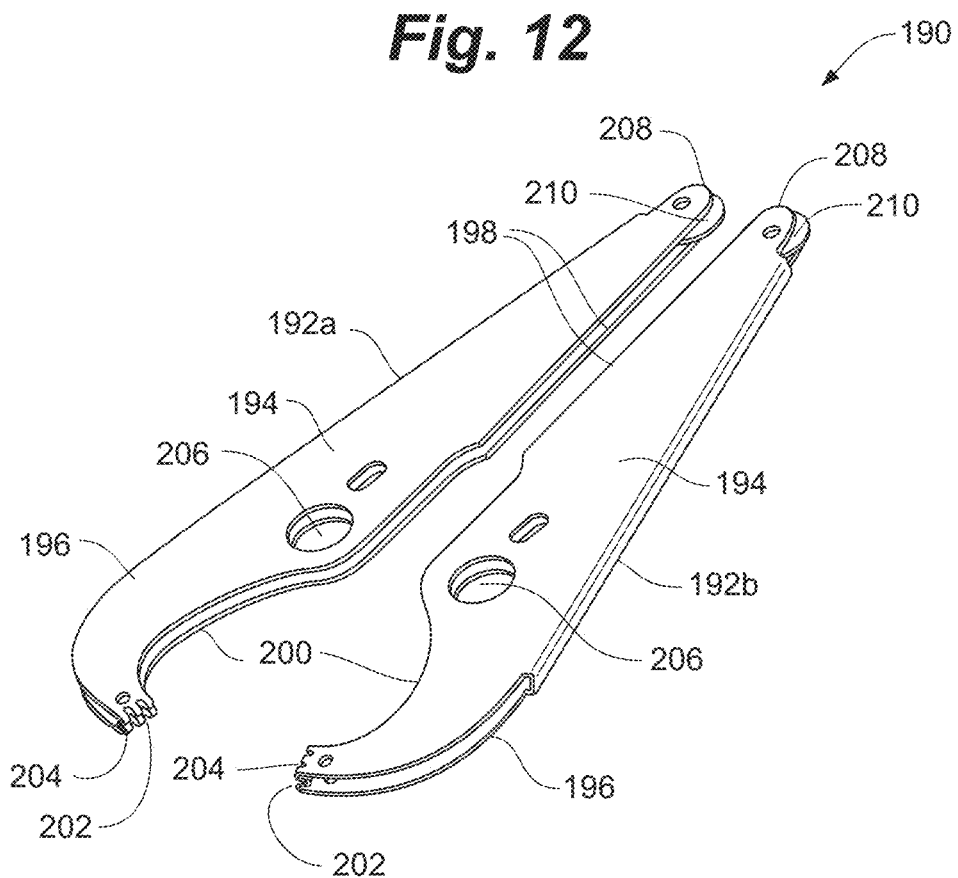
FIG. 12 is a top, perspective view of a sequential retention assembly of the skin fastening device of FIG. 4.

As seen in FIG. 12, skin fastening device 100 can further comprise a sequential retention assembly 190. Sequential retention assembly 190 generally comprises first and second approximation arms 192a, 192ba that are essentially mirror images of one another. Each of the first and second approximation arms 192a, 192b include an arm body 194 defined by an exterior wall 196, an interior engagement wall 198 and a retention wall 200. Exterior wall 196 and retention wall 200 are coupled at a grasping wall 202. Each grasping wall 202 can comprise one or more jaws or teeth 204. Each arm body 194 has a generally flat profile and includes an arm mounting aperture 206. In some embodiments, exterior wall 196 and interior engagement wall 198 can define a rounded engagement portion 208. In some embodiments, rounded engagement portion 208 can further include a rotatable engagement member 210. First and second approximation arms 192a, 192b can be fabricated of a rigid, nonflexible material to as to promote consistent retention of skin tissue with respect to head portion 120 of the skin fastening device 100. In some embodiments, the first and second approximation arms 192a, 192b can be fabricated from a medically compatible metal or metal alloy. In constructing the first and second approximation arms 192a, 192b of a suitable rigid, nonflexible material, a profile of the first and second approximation arms 192a, 192b can be reduced so as to enhance visibility of the fastening end 104 of the skin fastening device 100 during use in wound closure.

Referring again to FIGS. 11, skin fastening device 100 can further include a penetrator assembly 220 Generally penetrator assembly 220 can comprise a slidable body 222 having a driving end 224, a top surface 223, a bottom surface 225 and a fastening end 226. Proximate the driving end 224, the slidable body 222 can comprise a connection aperture 228 extending between the top surface 223 and the bottom surface 225. At the fastening end 226, the slidable body can comprise a pair of penetrator members 229a, 229b that are operably connected via an arcuate rear wall 230. Proximate the fastening end 226, the slidable body 222 can comprise one or more fastener windows 232 that extend through the slidable body 222.

Figure 13:
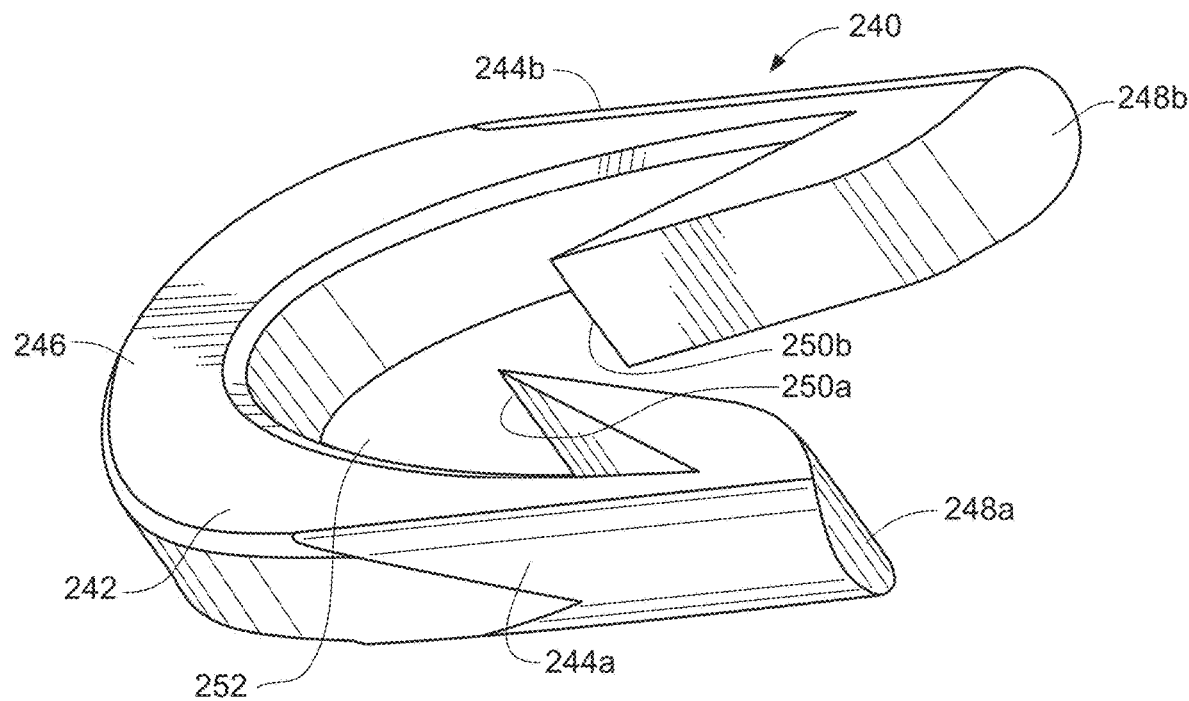
FIG. 13 is a top, perspective view of a fastener of the skin fastening device of FIG. 4.

Referring to FIG. 13, skin fastening device 100 generally includes one or more bioabsorbable fasteners or staples 240 such as, for example, those illustrated and described in U.S. Pat. Nos. 7,112,214 and 8,066,736, both of which are commercially available from the assignee of the present application, Incisive Surgical of Plymouth, MN. Fastener 240 generally comprises a fastener body 242 having a pair of staple arms 244a, 244b that are connected with an arcuate backspan 246. Each staple arm 244a, 244b can have a rounded tip 248a, 248b, from which a hook portion 250a, 250b can project inwardly so as to define a fastener capture area 252.

Figure 14:
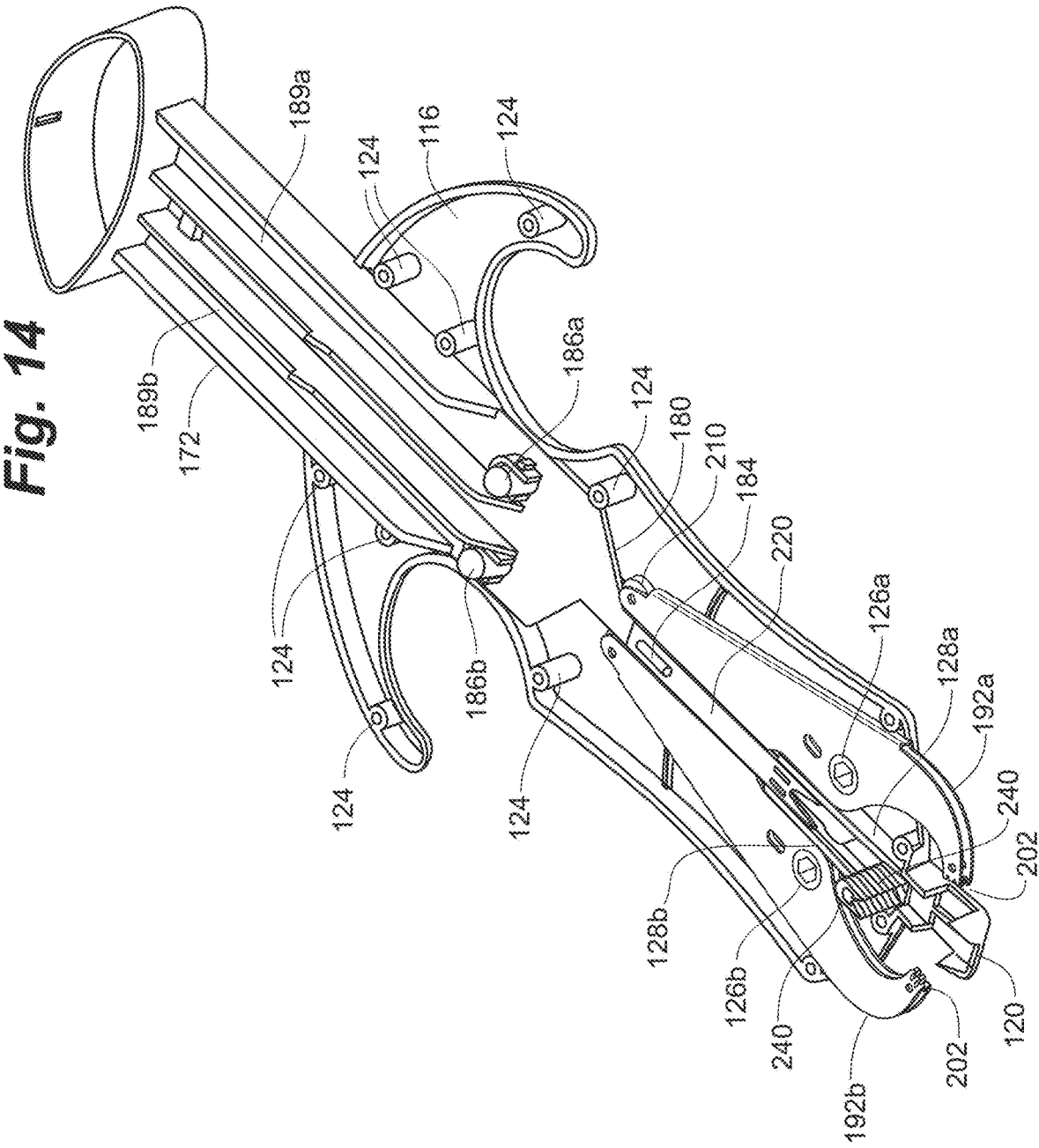
FIG. 14 is a bottom, perspective view of the skin fastening device of FIG. 4 with a lower housing member removed.
Figure 15:
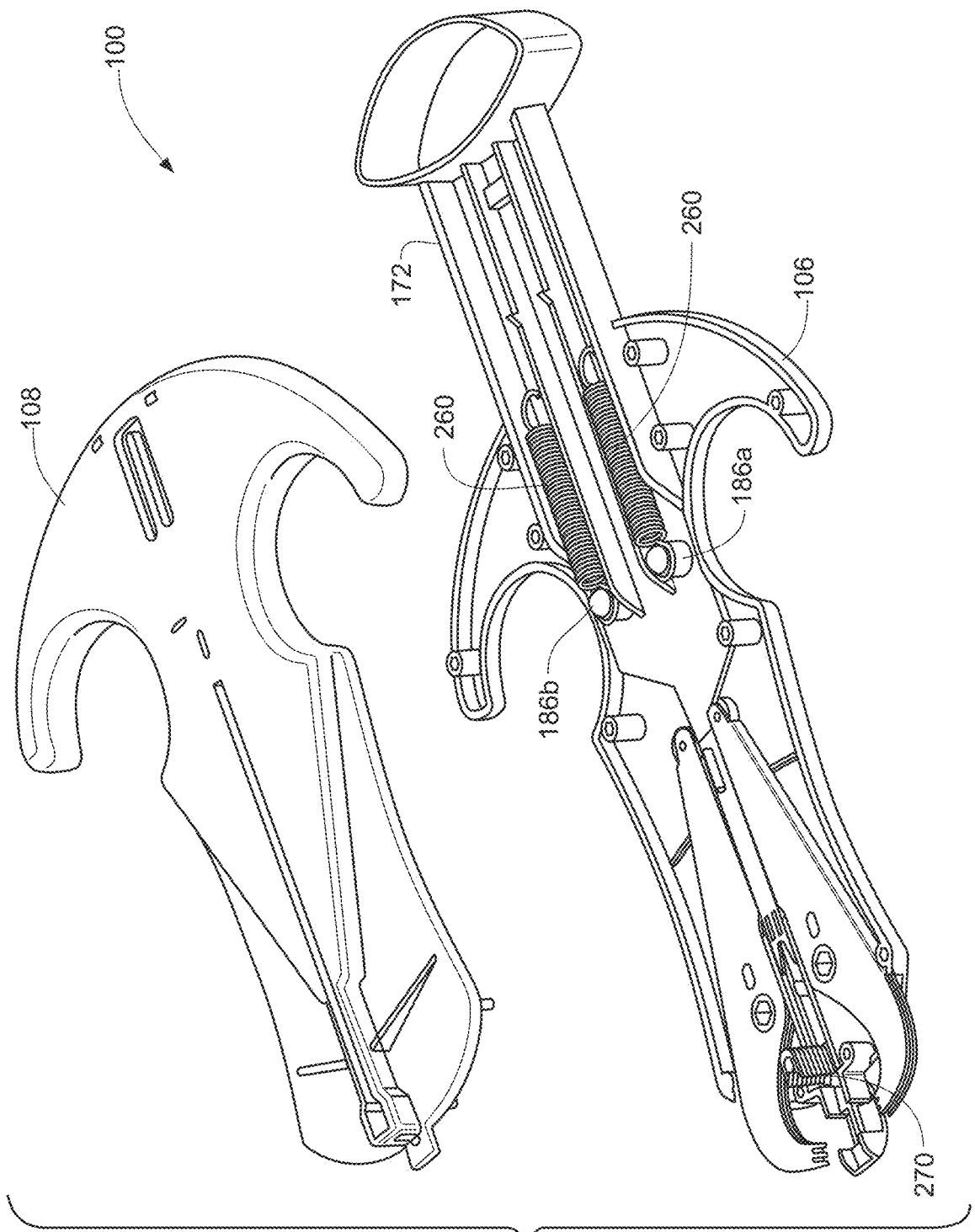
FIG. 15 is an exploded, bottom perspective view of the skin fastening device of FIG. 4.
Figure 16:
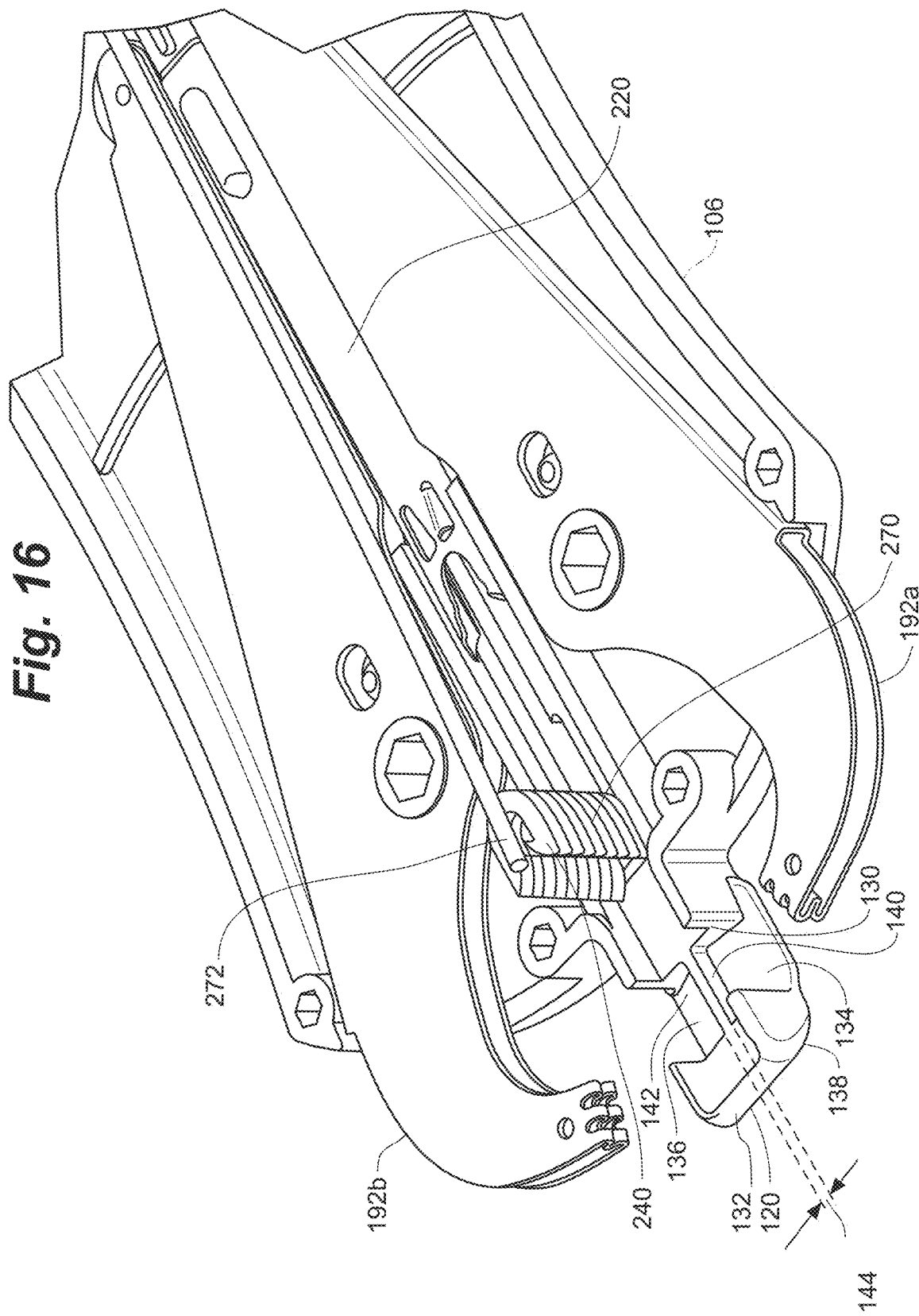
FIG. 16 is detailed, bottom perspective view of a fastening end of the fastening device of FIG. 4 with a lower housing member removed.

Assembly of skin fastening device 100 is described with specific reference to FIGS. 14, 15 and 16. Generally, the upper housing member 106 is positioned in an upside down position with the upper body surface 110 facing downward or being set on an assembly surface. Next, the actuator body 172 is placed on the downward facing surface 116 such that the upper actuator surface 178 is proximate the downward facing surface 116 and the actuator body 172 resides between the female connector members 124 as shown in FIG. 14. Next the penetrator assembly 220 can be positioned on the upper housing member 106 such that the top surface 223 is proximate the downward facing surface 116. The slidable body 222 is positioned such that the fastening end 226 resides within the guide walls 128a, 128b and the connection aperture 228 resides over the actuation projection 184 such that the penetrator assembly 220 is operably coupled to the actuator assembly 170. Next, the first and second approximation arms 192a, 192b of the sequential retention assembly 190 are positioned proximate the downward facing surface 116 such that each arm mounting aperture 206 is positioned over its corresponding mounting projection 126a, 126 such the first and second approximation arms 192a, 192b are rotatably coupled to the upper housing member 106. With the first and second approximation arms 192a, 192b rotatably coupled to the upper housing member 106, the rotatable engagement member 210 on the first approximation arm 192a is positioned against the first angled actuation surface 180 and the grasping walls 202 are positioned on their respective sides of the head portion 120 and consequently, their respective first and second retention zones 134, 136. Next, an actuation spring 260 is positioned within each of the actuation channels 189a, 189b with one end of the actuation spring 260 coupled to the corresponding actuator projection 186a, 186b as shown in FIG. 15. Next, the lower housing member 108 is oriented such that the upward facing surface 150 is facing the downward facing surface 116 and the lower gripping members 152a, 152b are aligned with their corresponding upper gripping member 118a, 118b. The lower housing member 108 is brought into contact with the upper housing member 108 such that the male connector members 160 are inserted into the corresponding female connector members 124 whereby the upper and lower housing members 106, 108 are joined to form the device body 102 with the actuator assembly 170, sequential retention assembly 190 and penetrator assembly 220 operably linked within the device body 102. Finally, the fasteners 240, typically as a fastener stack 270 comprising a plurality of fasteners 240, are inserted into the fastener stack aperture 154 followed by a fastener spring or tension rod 272 for biasing the fastener stack 270 within the fastener stack aperture 154. At this point, skin fastening device 100 is ready for use by a medical professional.

Figure 17:
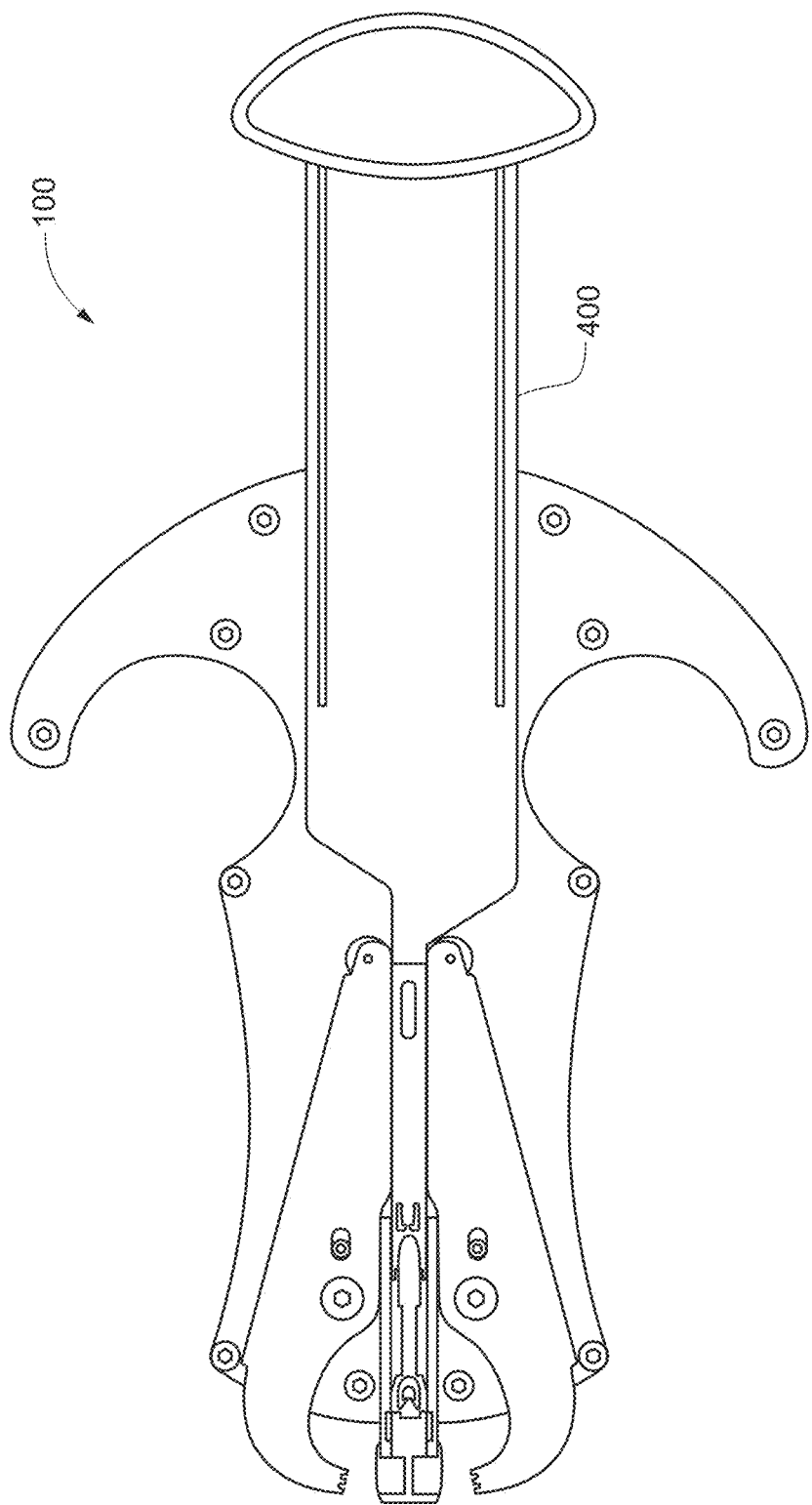
FIG. 17 is a bottom view of the fastening device of FIG. 4 with a lower housing member removed and in a ready orientation.
Figure 18:
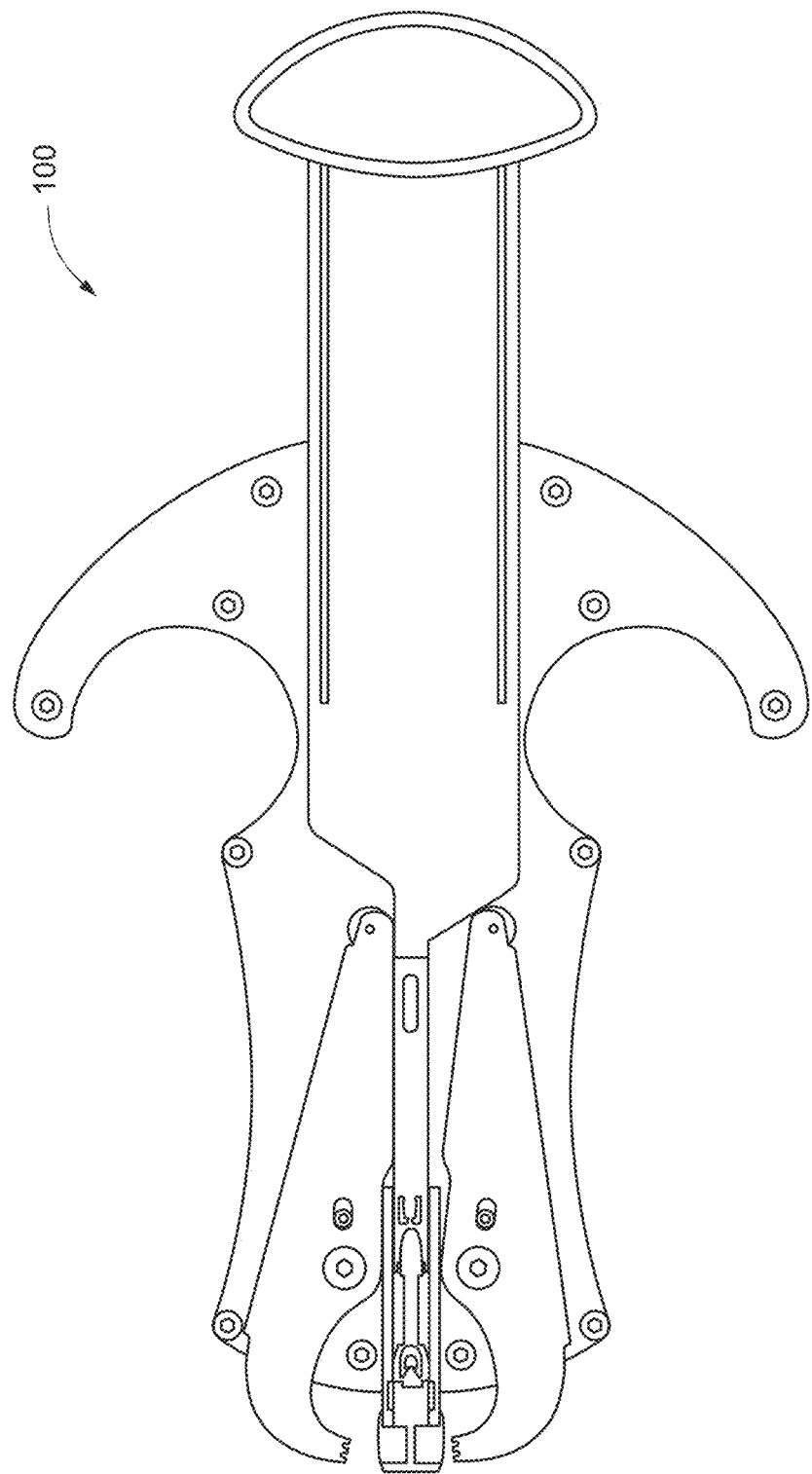
FIG. 18 is a bottom view of the fastening device of FIG. 4 with a lower housing member removed.
Figure 19:
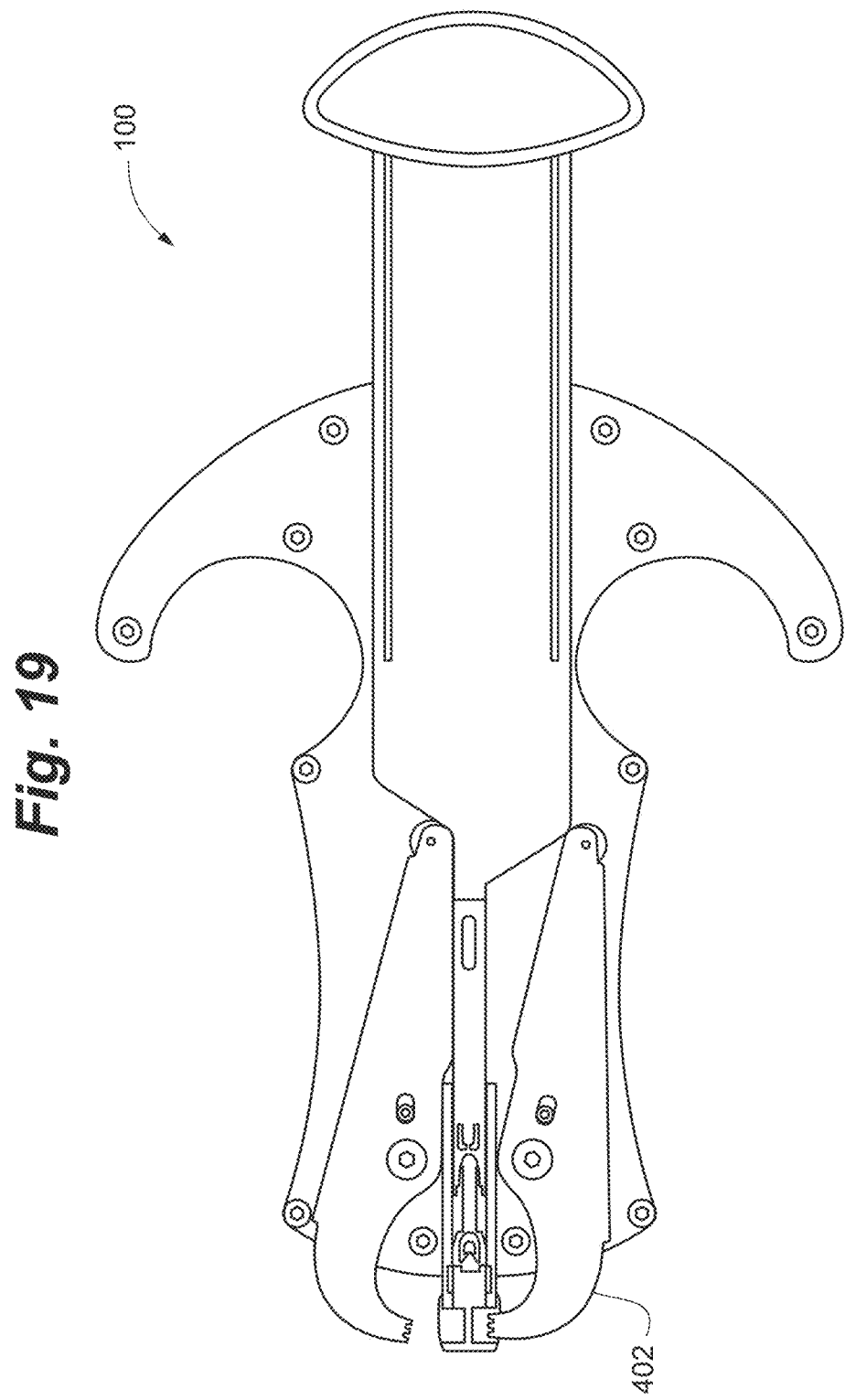
FIG. 19 is a bottom view of the fastening device of FIG. 4 with a lower housing member removed and in a first retention position
Figure 23:
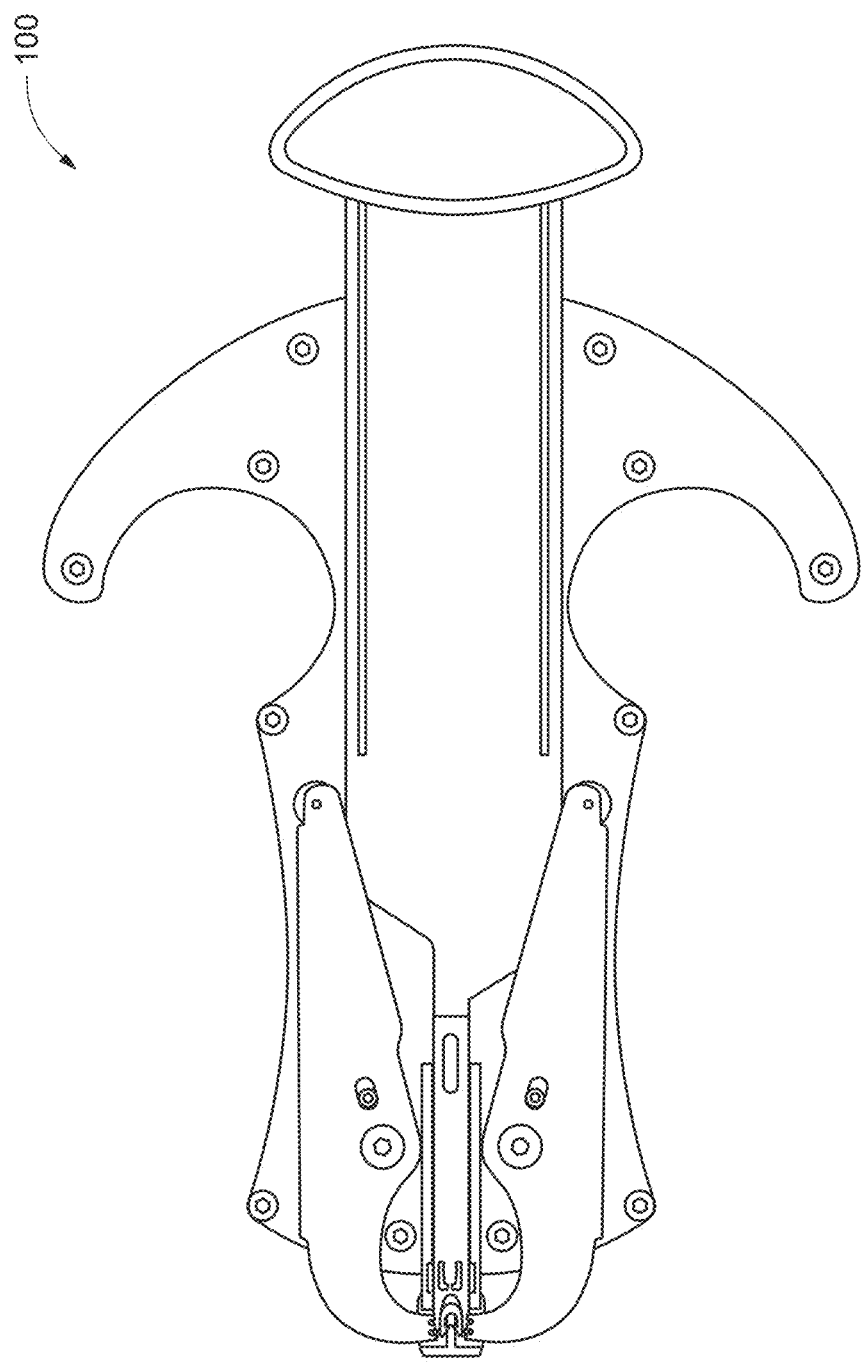
FIG. 23 is a bottom view of the fastening device of FIG. 4 with a lower housing member removed.
Figure 24:
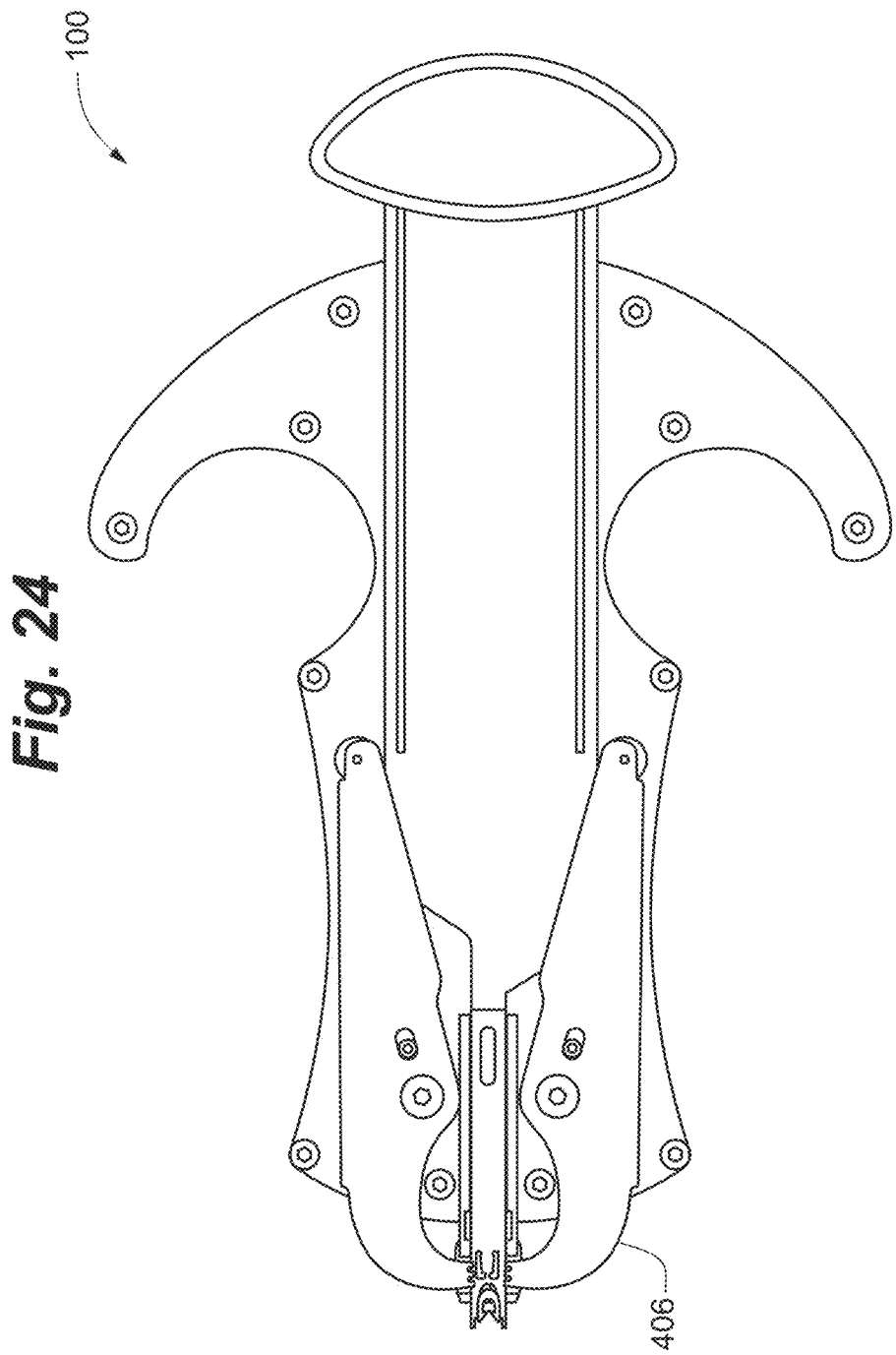
FIG. 24 is a bottom view of the fastening device of FIG. 4 with a lower housing member removed and in a fastener placement disposition
Figure 25:
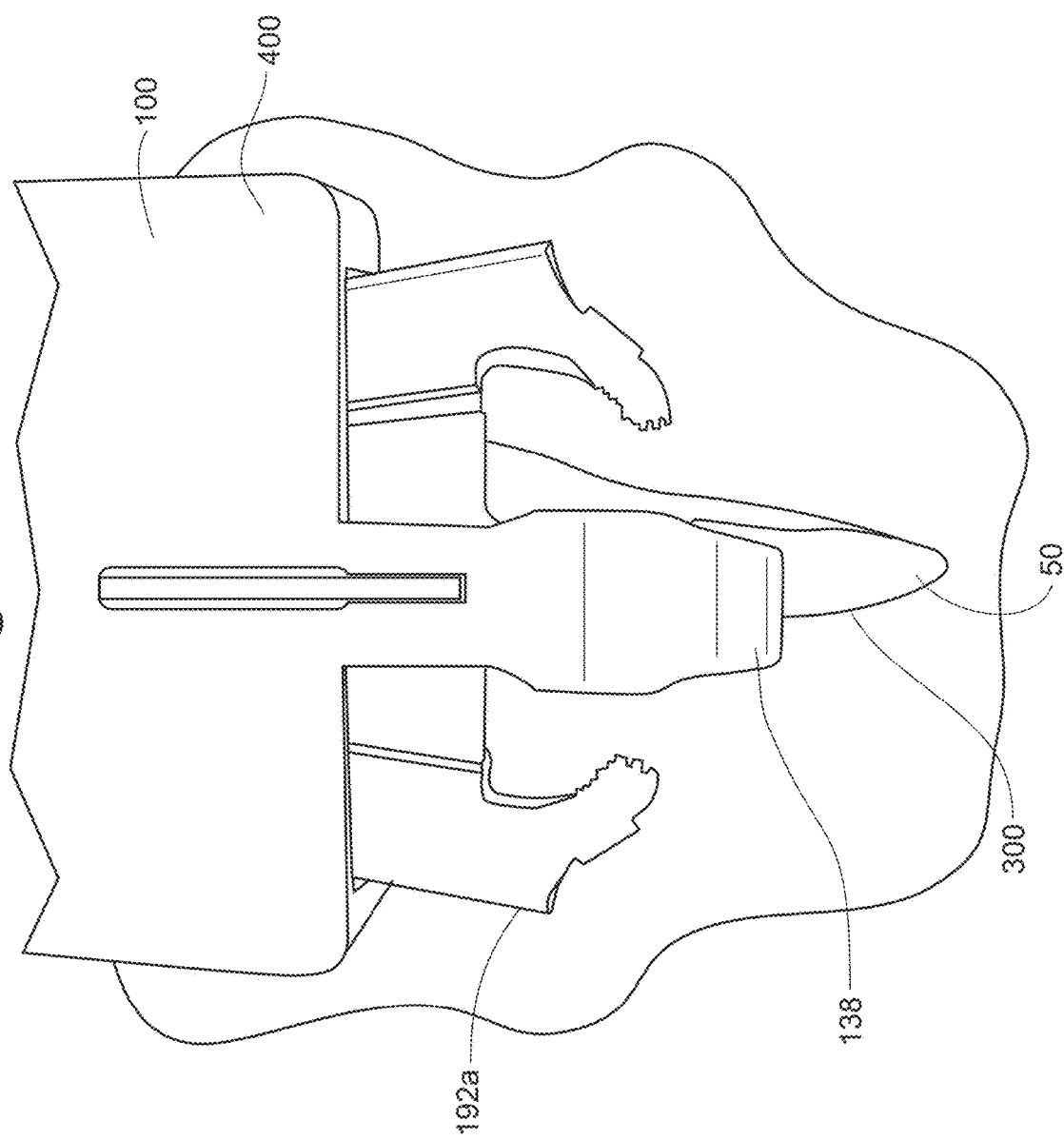
FIG. 25 is a top view of a skin opening having a head portion of the fastening device of FIG. 4 positioned there within.
Figure 26:
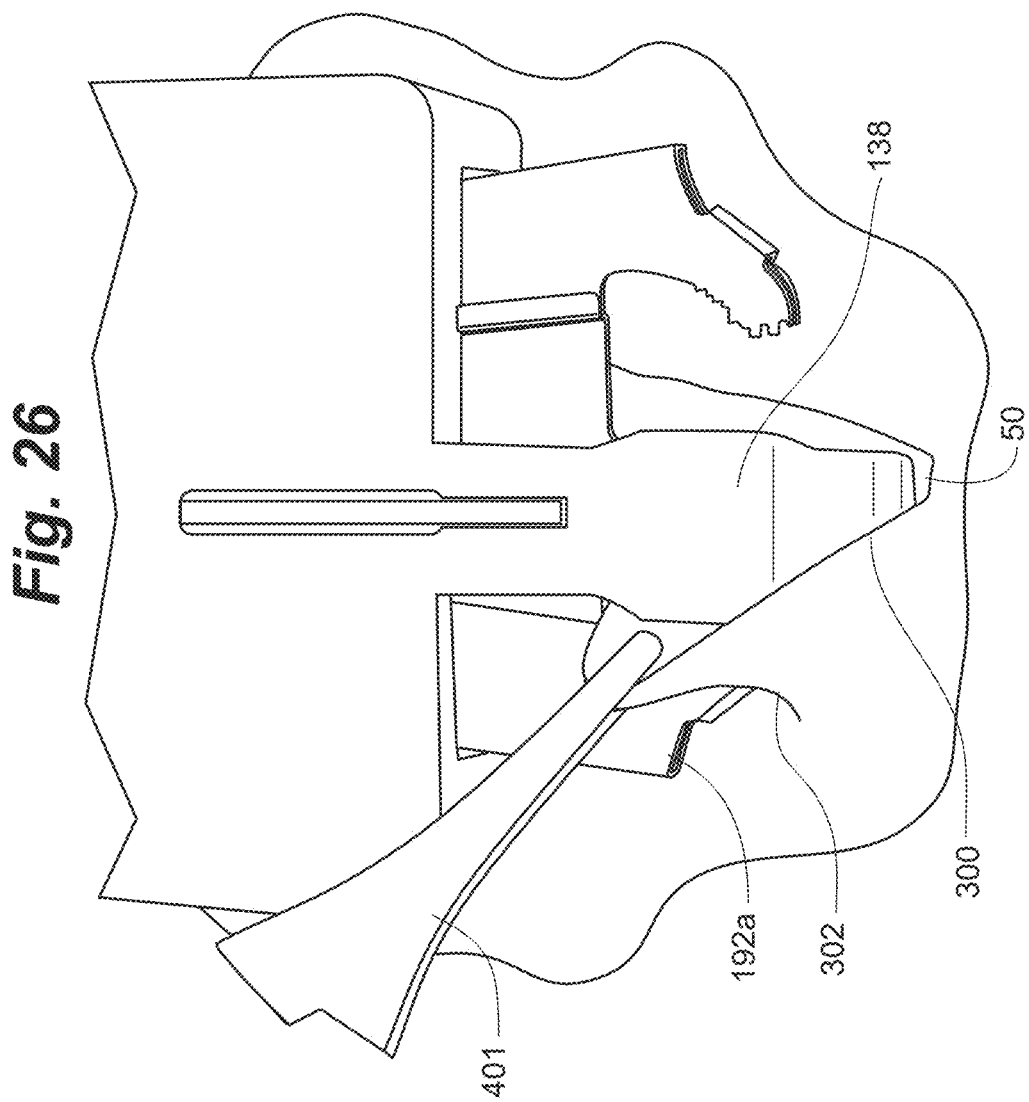
FIG. 26 is a top view of the skin opening of FIG. 25 having a first skin side being captured by the fastening device of FIG. 4.
Figure 27:
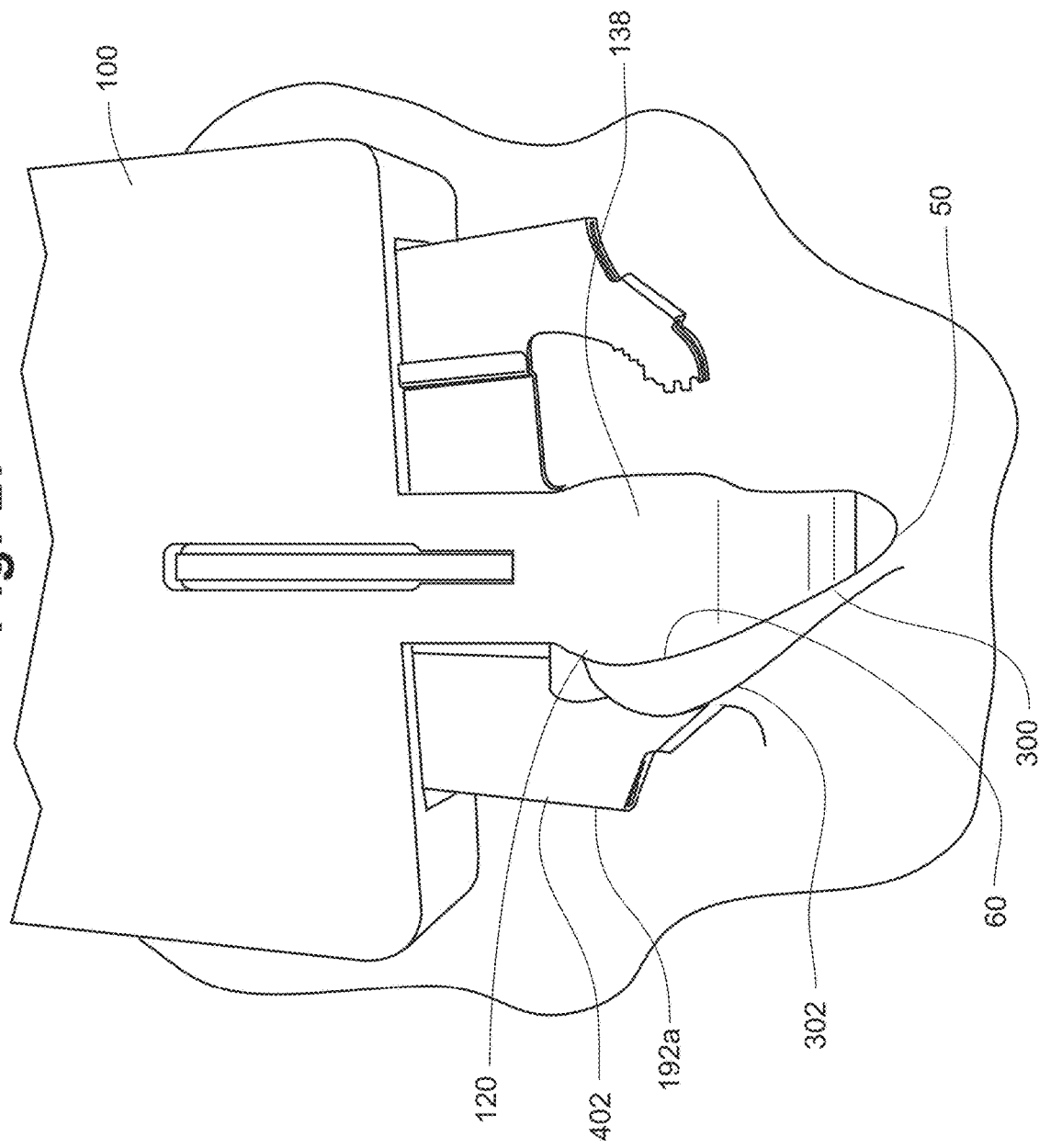
FIG. 27 is a top view of the skin opening of FIG. 25 with a first skin side being captured by the fastening device of FIG. 4 in a first retention position.

Operation of skin fastening device 100 is shown in FIGS. 17-24 in which the lower housing member 108 is removed for ease of illustration and retention of skin tissue is not shown for purposes of clarity. Skin retention during operation of fastening device 100 is illustrated within FIGS. 25-30. In use, the skin fastening device 100 in a ready orientation 400 as seen in FIG. 17 is oriented such that the head body 138 can be positioned within skin opening 50 and the first retention zone 134 can be placed against the inner surface 60 of a first side 300 of skin opening 50 as shown in FIG. 25. The user begins pressing down on the handle portion 178 such that the actuator body 172 begins advancing into the device body 102. As the actuator body 172 slides into the device body 102, the slidable body 222 is directed toward the head portion 102. At the same time, the rotatable engagement member 210 on the first approximation arm 192a comes into contact with the first angled actuation surface 180 as illustrated in FIG. 18. As the advancement of the actuator body 172 continues, the rotatable engagement member 210 moves along the first angled actuation surface 180 such that the first approximation arm 192a is cause to rotate around mounting projection 126a, thereby resulting in grasping wall 202 and teeth 204 approaching and grasping an exterior surface 302 of the first side 300 of skin opening 50 as shown in FIG. 26. As illustrate in FIG. 26, a medical professional can utilize an instrument such as, for example, a forceps 401 to assist with positioning first side 300 relative to the head body 138. As the first approximation arm 192a, continues its rotation, the grasping wall 202 and teeth 204 position and force the inner surface 60 of the first side 300 into the first retention zone 134 such that the first side 300 is positioned and retained against the head portion 120 with the fastening device 100 in a first retention position 402 as shown in FIGS. 19 and 27.

Figure 20:
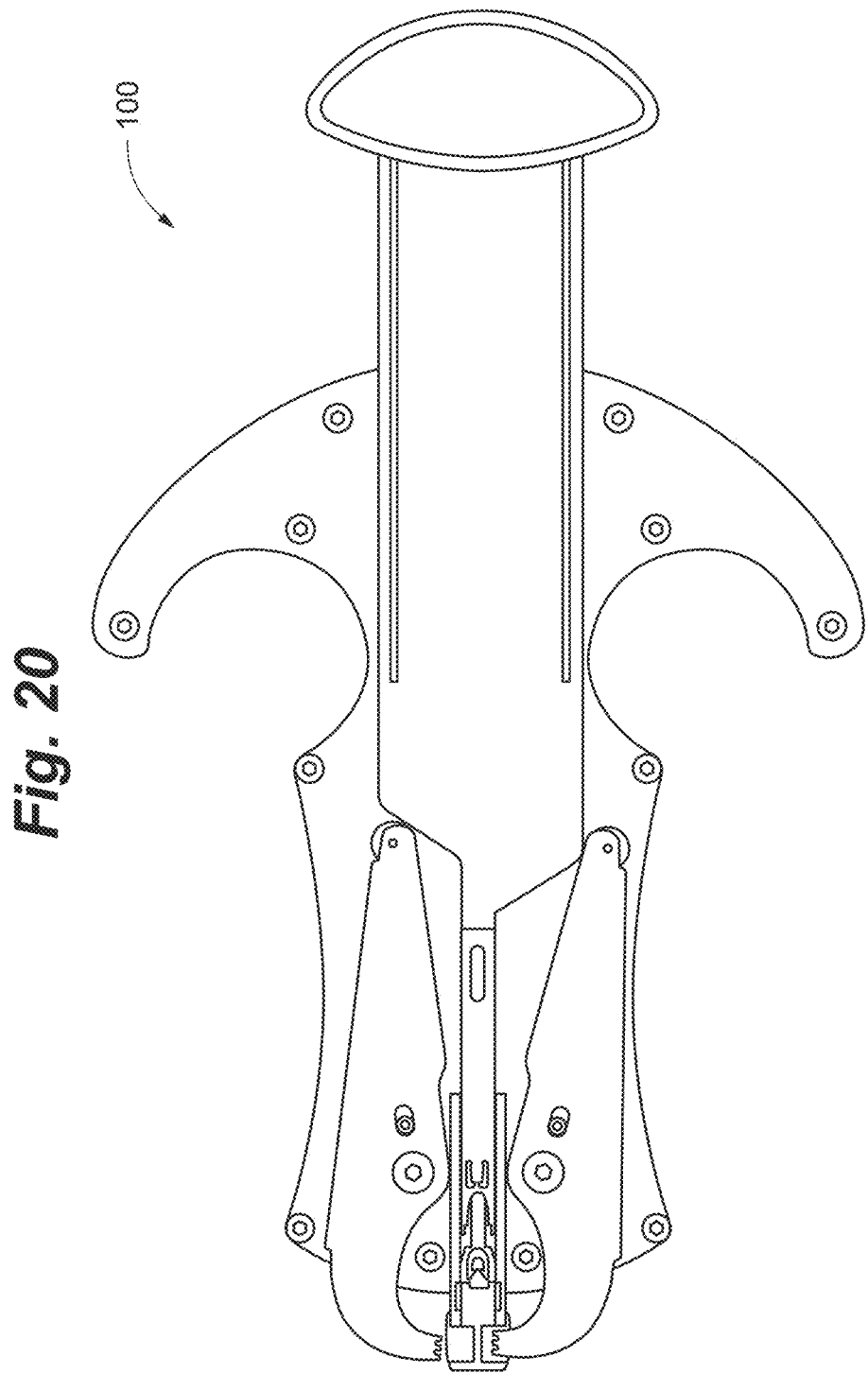
FIG. 20 is a bottom view of the fastening device of FIG. 4 with a lower housing member removed.
Figure 21:
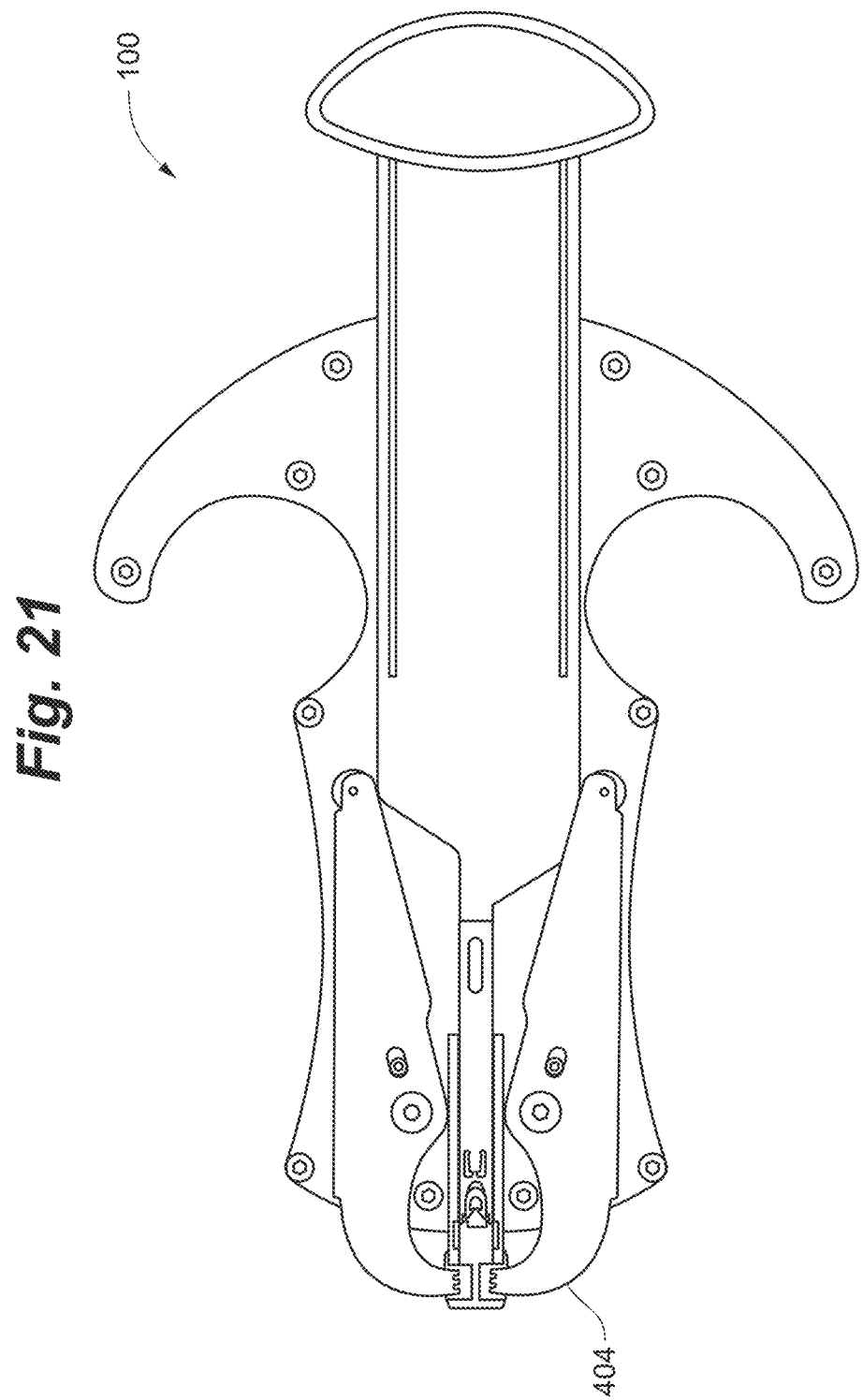
FIG. 21 is a bottom view of the fastening device of FIG. 4 with a lower housing member removed and in a second retention position.
Figure 28:
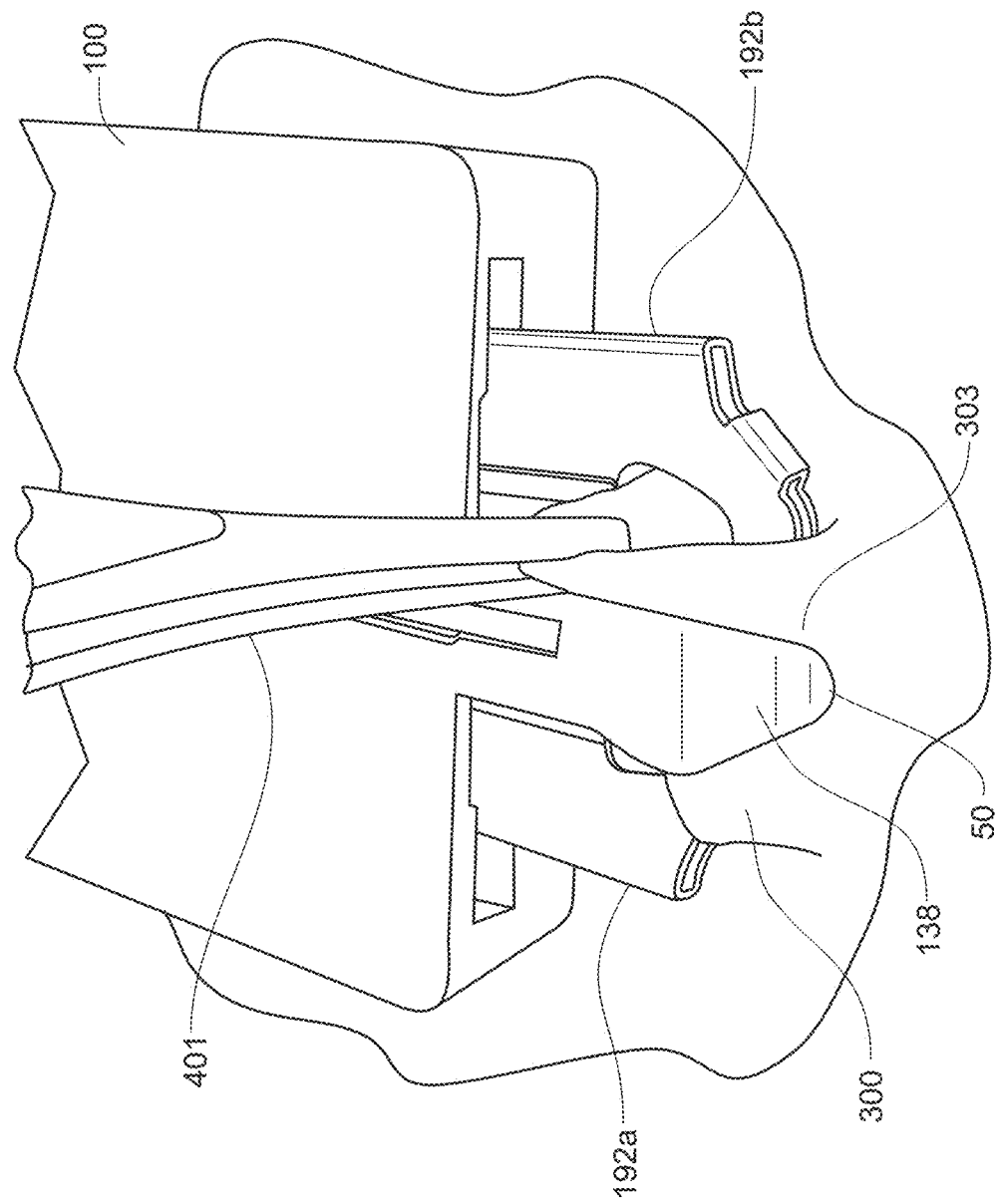
FIG. 28 is a top view of the skin opening of FIG. 25 with a second skin side being captured by the fastening device of FIG. 4.
Figure 29:
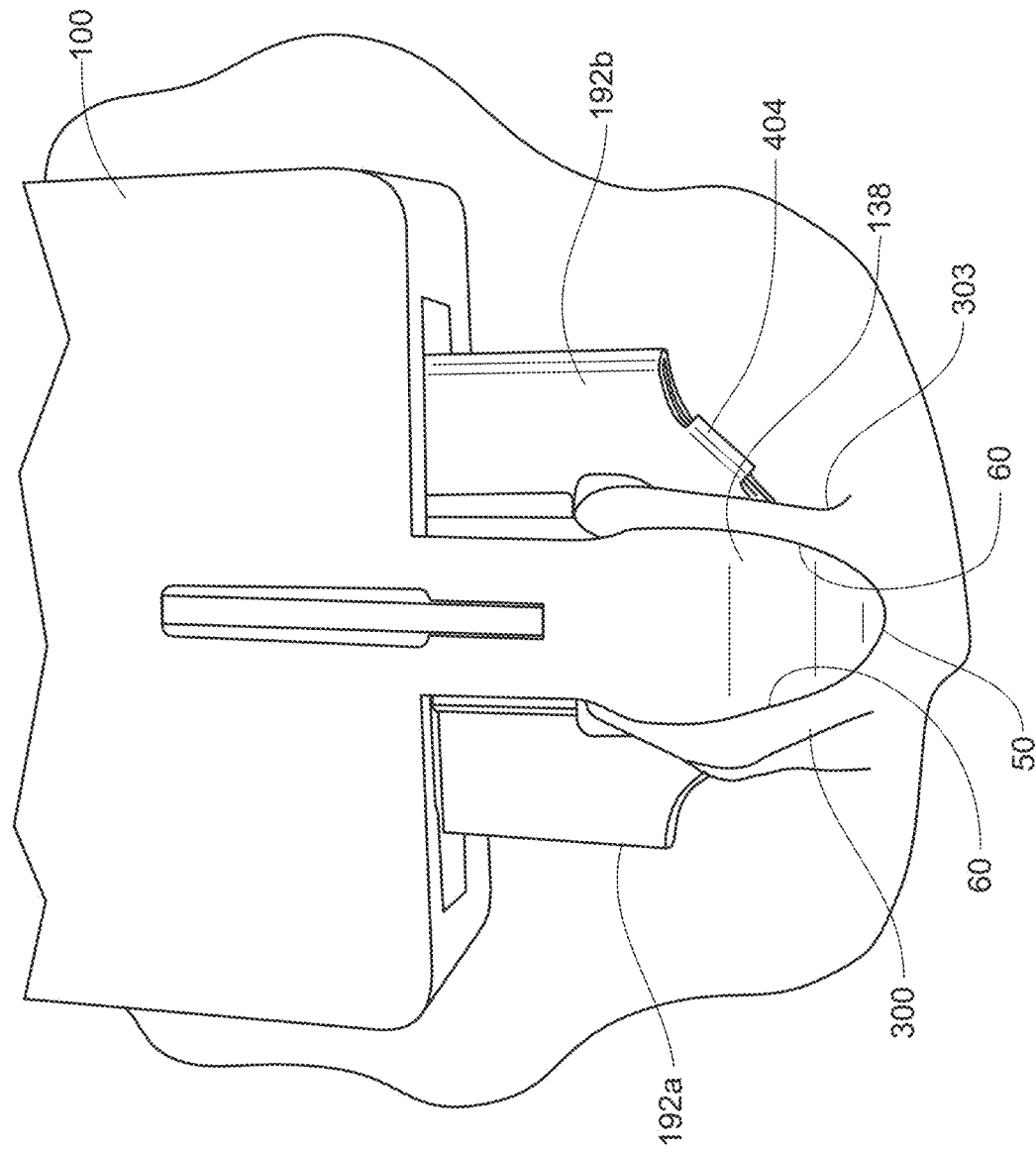
FIG. 29 is a top view of the skin opening of FIG. 25 with a second skin side being captured by the fastening device of FIG. 4 in a second retention position.

With the first side 300 retained and positioned with respect to the head portion 120, the head body 138 is repositioned such that second retention zone 136 is placed against the inner surface 60 of a second side 303 of skin opening 50 as shown in FIG. 28. Once again, the medical professional can utilize forceps 401 to assist in positioning second side 303 relative to the head body 138. The user again presses down on handle portion 178 such that the actuator body 172 is advanced further into the device body 102. The rotatable engagement member 210 on the second approximation arm 192b comes into contact with the second angled actuation surface 182, thereby causing the second approximation arm 192b to rotate around the mounting projection 126b as shown in FIG. 20. As the second approximation arm 192b rotates, the grasping wall 202 and teeth 204 position and force the inner surface 60 of the second side 303 into the second retention zone 136. Second side 303 is positioned and retained against the head portion 120 in a second retention position 404 as shown in FIGS. 21 and 29.

Figure 22:
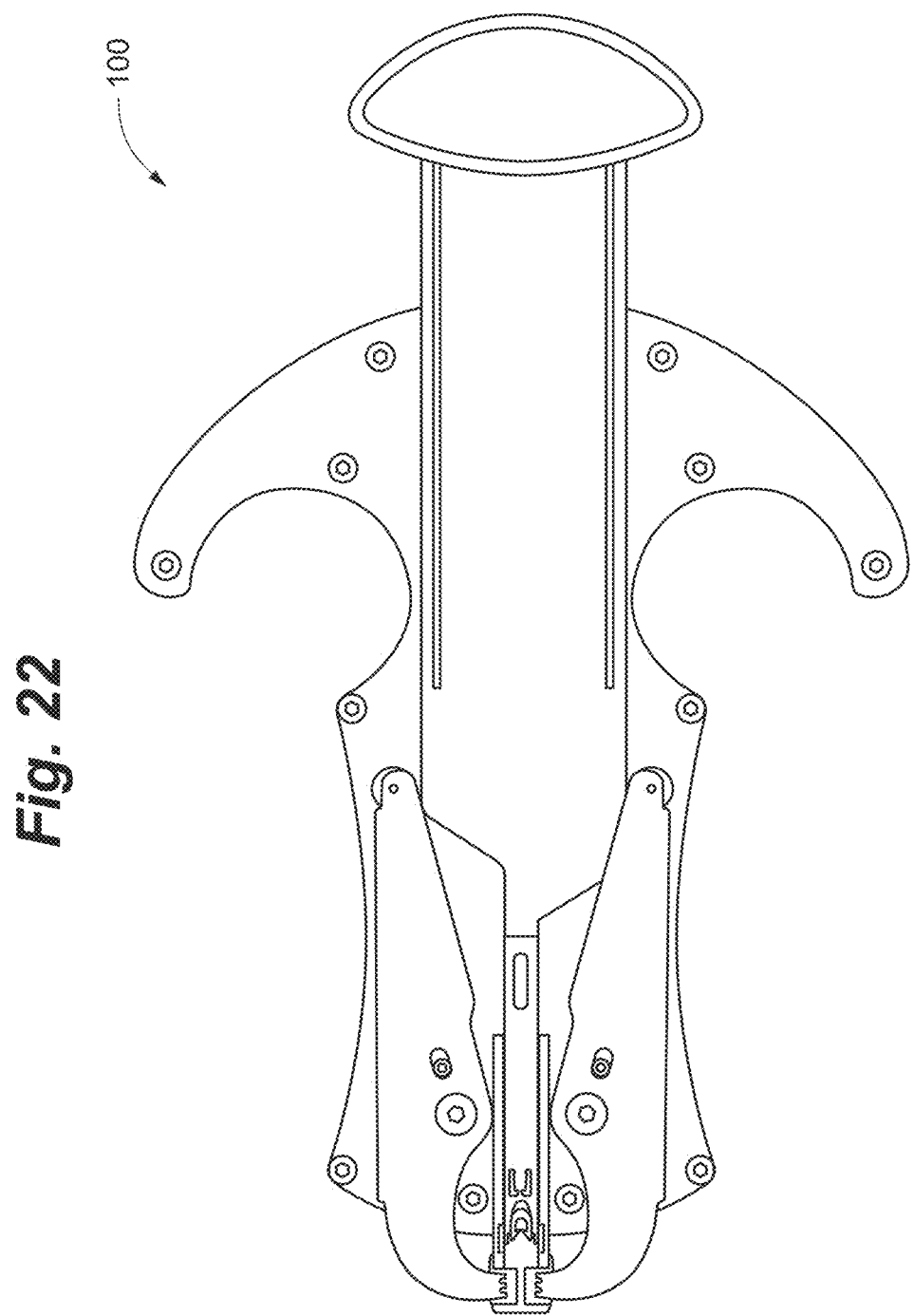
FIG. 22 is a bottom view of the fastening device of FIG. 4 with a lower housing member removed.

As the first and second approximation arms 192a, 192b are caused to rotate in response to contact with the actuator body 172, the interaction of the connection aperture 228 with the actuation projection 184 causes the penetrator assembly 220 to be directed toward the head portion 120 as shown in FIG. 22. As the penetrator assembly 220 advances forward, a bottommost fastener 240 of the fastener stack 270 is collected between the penetrators 228a, 228b and the arcuate rear wall 230 as shown in FIG. 23. Continued pressing of the handle portion 178 causes the penetrator assembly 220, now carrying the fastener 240, toward the head portion 120. Penetrators 228a, 228b are advanced into and through the dermal layer 56 of the first and second sides 300, 302 that are positioned within first retention zone 134 and second retention zone 136 respectively. As the penetrators 228a, 228b are driven through the dermal layer 56, the corresponding staple arms 244a, 244b are carried through the pierced openings created by the penetrators 228a, 228b when the skin fastening device 100 is in a fastener placement disposition 406 as shown in FIG. 24.

Finally, handle portion 178 is retracted or otherwise withdrawn from the device body 102 whereby the interaction of the penetrator assembly 220 with the actuator body 172 causes the penetrators 228a, 228b to be withdrawn back into the device body 102. As the penetrators 228a, 228b are pulled back through the pierced opening in the dermal tissue of first side 300 and second side 302, the first and second sides 300 and 302 are captured within the hook portions 250a, 250b of fastener 240 and fastener 240 remains in position within the opening 50 as the penetrators 228a, 228b withdraw into device body 102. Further withdrawal of the handle portion 178 allows the first and second approximation arms 192a, 192b to sequentially rotate into their open positions as the actuator body 172 disengages from the rotatable engagement members 210 such that the device body reassumes the ready orientation 400 prior to deployment of the next fastener 240 as shown in FIG. 30. This process can be repeated along the length of skin opening 50 to deploy multiple fasteners 240.

The sequential operation of the first and second approximation arms 192a, 192b provide an advantage over the prior art in that the tissue retention process is easily accomplished by a single person as the user need only focus on positioning one tissue side at a time. Furthermore, the sequential operation of the first and second approximation arms is especially beneficial in closing small tissue openings in which positioning of the head portion 120 with respect to first and second side 302 can be difficult. Finally, the nature of the skin fastening device 100 allows for the placement of fasteners 240 in a range of orientations including parallel, oblique, and perpendicular with respect an exterior skin surface at the skin opening 50. In addition, the reduced profile of the head portion 120 and tissue approximation arms 192a, 192b enhance an overhead view of the skin fastening device 100 during wound closure. Finally, the skin fastening device 100 can be utilized in conjunction with one or more wound closure techniques for example, traditional metallic staplers or the INSORB® Skin Closure System, to close a full length of a skin wound wherein the reduced profile of the skin fastening device 100 allows for use at end regions of a longer wound that would be otherwise difficult to close with conventional techniques. For instance, the skin fastening device of the present invention can be utilized to deliver fasteners into end portions that are less than 2 cm in length. In addition, the skin fastening device of the present invention can be manipulated so as to delivery fasteners in parallel, perpendicular or oblique orientations relative to an exterior surface of skin.

Although specific examples have been illustrated and described herein, it will be appreciated by those of ordinary skill in the art that the present application is intended to cover adaptations or variations thereof of the presently disclosed invention. Therefore, it will be understood that the scope of the present invention is defined by the attached claims and their legal equivalents.

The invention claimed is:

1. A method for securing skin tissue with a fastener, comprising:
    placing a head portion of a fastening device within a skin wound;
    positioning a first side of skin tissue between a first approximation arm and the head portion;
    retaining the first side of skin tissue between the first approximation arm and the head portion;
    positioning a second side of skin tissue between a second approximation arm and the head portion while the first side of skin tissue remains retained;
    retaining the second side of skin tissue between the second approximation arm and the head portion;
    delivering a fastener into the retained first and second sides of skin tissue;
    wherein positioning the first side of skin tissue, comprises:
        grasping the first side of skin tissue with a forceps; and
        placing the first side of skin tissue in close proximity to the head portion.

2. The method of claim 1, wherein the skin wound has a wound length less than about 2 cm.

3. The method of claim 1, further comprising:
grasping the second side of skin tissue with the forceps, while the first side of skin tissue remains retained;
placing the second side of skin tissue in close proximity to the head portion.

4. The method of claim 1, wherein delivering the fastener into the retained first and second sides of skin tissue, further comprises:
inserting a staple arm into each of the first and second sides of skin tissue such that a backspan resides across a vertical interface defined along a length of the skin wound between the first and second sides of skin tissue.

5. The method of claim 1, wherein retaining the first side of skin tissue between the first approximation arm and the head portion, further comprises:
advancing an actuator body on the fastening device such that the actuator body contacts the first approximation arm such that the first approximation arm rotatably positions the first side of skin tissue against the head portion.

6. The method of claim 5, wherein retaining the second side of skin tissue between the second approximation arm and the head portion, further comprises:
advancing the actuator body such that the actuator body contacts the second approximation arm such that the second approximation arm rotatably positions the second side of skin tissue against the head portion.

7. The method of claim 6, wherein delivering the fastener into the retained first and second sides of skin tissue, further comprises:
advancing the actuator body such that the actuator body directs a penetrator into each of the retained first and second sides of skin tissue, whereby a pierced opening is formed in each of the retained first and second sides of skin tissue; and
deploying the fastener by carrying a staple arm through each of the pierced openings in the first and second sides of skin tissue.

8. The method of claim 1, wherein the fastening device resides at a parallel, oblique or perpendicular orientation with respect to the skin wound.

9. The method of claim 1, wherein the skin wound is selected from the group consisting essentially of: a linear incision, a skin port, a tissue excision and an irregular laceration.

10. A skin fastening device performing the method of claim 1.

11. A method for securing skin tissue with a fastener, comprising:
placing a head portion of a fastening device within a skin wound;
positioning a first side of skin tissue between a first approximation arm and the head portion;
retaining the first side of skin tissue between the first approximation arm and the head portion;
positioning a second side of skin tissue between a second approximation arm and the head portion while the first side of skin tissue remains retained;
retaining the second side of skin tissue between the second approximation arm and the head portion;
delivering a fastener into the retained first and second sides of skin tissue;
wherein retaining the first side of skin tissue between the first approximation arm and the head portion, further comprises:
advancing an actuator body on the fastening device such that the actuator body contacts the first approximation arm such that the first approximation arm rotatably positions the first side of skin tissue against the head portion.

12. The method of claim 11, wherein retaining the second side of skin tissue between the second approximation arm and the head portion, further comprises:
advancing the actuator body such that the actuator body contacts the second approximation arm such that the second approximation arm rotatably positions the second side of skin tissue against the head portion.

13. The method of claim 12, wherein delivering the fastener into the retained first and second sides of skin tissue, further comprises:
advancing the actuator body such that the actuator body directs a penetrator into each of the retained first and second sides of skin tissue, whereby a pierced opening is formed in each of the retained first and second sides of skin tissue; and
deploying the fastener by carrying a staple arm through each of the pierced openings in the first and second sides of skin tissue.

14. The method of claim 11, wherein delivering the fastener into the retained first and second sides of skin tissue, further comprises:
inserting a staple arm into each of the first and second sides of skin tissue such that a backspan resides across a vertical interface defined along a length of the skin wound between the first and second sides of skin tissue.

* * * * *

UNITED STATES PATENT AND TRADEMARK OFFICE
CERTIFICATE OF CORRECTION

| | |
|---|---|
| PATENT NO. | : 12,042,149 B2 |
| APPLICATION NO. | : 17/323220 |
| DATED | : July 23, 2024 |
| INVENTOR(S) | : James A. Peterson et al. |

Page 1 of 1

It is certified that error appears in the above-identified patent and that said Letters Patent is hereby corrected as shown below:

On the Title Page

Column 1, (Item (60) Related U.S. Application Data), Line 1, delete "Continuation of" and insert -- Division of --

Column 2, (Item (56) Other Publication), Line 1, delete "Suture$^{ADDAC;AGO}$" and insert -- Sutureò --

Page 2

Column 1, (Item (60) Related U.S. Application Data), Line 1, delete "division of" and insert -- continuation of --

Signed and Sealed this
Third Day of September, 2024

Katherine Kelly Vidal
*Director of the United States Patent and Trademark Office*